United States Patent
Niehrs et al.

(10) Patent No.: US 8,921,056 B2
(45) Date of Patent: Dec. 30, 2014

(54) COMPOSITIONS FOR DIAGNOSIS AND THERAPY OF DISEASES ASSOCIATED WITH ABERRANT EXPRESSION OF FUTRINS (R-SPONDINS) AND/OR WNT

(71) Applicant: Deutsches Krebsforschungszentrum, Heidelberg (DE)

(72) Inventors: Christof Niehrs, Heidelberg (DE); Wei Wu, Beijing (CN); Andrey Glinka, Edingen-Neckarhausen (DE); Olga Kazanskaya, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 14/245,807

(22) Filed: Apr. 4, 2014

(65) Prior Publication Data

US 2014/0227713 A1    Aug. 14, 2014

Related U.S. Application Data

(60) Continuation of application No. 13/951,152, filed on Jul. 25, 2013, which is a division of application No. 13/931,481, filed on Jun. 28, 2013, which is a division of application No. 10/575,217, filed as application No. PCT/EP2004/011269 on Oct. 8, 2004.

(30) Foreign Application Priority Data

Oct. 10, 2003    (EP) ..................... 03023000

(51) Int. Cl.
  *C12Q 1/68*  (2006.01)
  *C12Q 1/66*  (2006.01)
  *C12N 9/00*  (2006.01)

(52) U.S. Cl.
  USPC .......... 435/7.21; 435/6.13; 435/8; 435/320.1; 536/24.1

(58) Field of Classification Search
  CPC .... C12Q 1/6897; C12Q 1/00; G01N 33/5008; G01N 33/582; G01N 2500/10; C07K 14/435; C07K 16/18
  See application file for complete search history.

(56) References Cited

U.S. PATENT DOCUMENTS

| | | | |
|---|---|---|---|
| 6,485,972 B1 | 11/2002 | McMahon et al. |
| 6,653,448 B1 | 11/2003 | Vernet et al. |
| 6,824,973 B2 | 11/2004 | Tang et al. |
| 7,319,141 B2 | 1/2008 | Tang et al. |
| 7,320,880 B2 | 1/2008 | Nishikawa et al. |
| 7,411,052 B2 | 8/2008 | Tang |
| 7,439,327 B2 | 10/2008 | Boyle et al. |
| 7,439,332 B2 | 10/2008 | Nishikawa |
| 7,541,431 B2 | 6/2009 | Yoon |
| 7,674,890 B2 | 3/2010 | Boyle et al. |
| 7,951,381 B2 | 5/2011 | Funk et al. |
| 8,088,374 B2 | 1/2012 | Niehrs et al. |
| 8,158,757 B2 | 4/2012 | Gurney et al. |
| 8,158,758 B2 | 4/2012 | Gurney |
| 8,540,989 B2 | 9/2013 | Gurney |
| 2001/0055790 A1 | 12/2001 | Barnes et al. |
| 2002/0065394 A1 | 5/2002 | Jacobs et al. |
| 2003/0017480 A1 | 1/2003 | Ota et al. |
| 2003/0022217 A1 | 1/2003 | Ceccardi et al. |
| 2003/0022255 A1 | 1/2003 | Morris et al. |
| 2003/0044792 A1 | 3/2003 | Tang et al. |
| 2003/0198975 A1 | 10/2003 | Azimzai et al. |
| 2004/0077048 A1 | 4/2004 | Warren et al. |
| 2005/0054829 A1 | 3/2005 | Wiley et al. |
| 2007/0244061 A1 | 10/2007 | Niehrs et al. |
| 2009/0036369 A1 | 2/2009 | Kakitani et al. |
| 2009/0118176 A1 | 5/2009 | Emtage et al. |
| 2010/0278800 A1 | 11/2010 | Boyle et al. |
| 2011/0091454 A1 | 4/2011 | Diber et al. |
| 2012/0039912 A1 | 2/2012 | Rawadi et al. |
| 2012/0263730 A1 | 10/2012 | Niehrs et al. |
| 2013/0095116 A1 | 4/2013 | Gurney et al. |
| 2013/0115206 A1 | 5/2013 | Gurney et al. |
| 2013/0121993 A1 | 5/2013 | Gurney et al. |

FOREIGN PATENT DOCUMENTS

| | | |
|---|---|---|
| EP | 1 427 747 | 4/2012 |
| WO | 98/41539 | 9/1998 |
| WO | 98/49302 | 11/1998 |
| WO | 01/77169 | 10/2001 |
| WO | 03/025142 | 3/2003 |
| WO | 03/027230 | 4/2003 |
| WO | 03/094843 | 11/2003 |
| WO | 2004/080148 | 9/2004 |
| WO | 2004/099408 | 11/2004 |
| WO | 2006/104536 | 10/2006 |

OTHER PUBLICATIONS

Bienz et al., "Linking Colorectal Cancer to Wnt Signaling" Cell 103:311-320 ( 2000).
Brantjes et al., "TCF: Lady Justice Casting the Final Verdict on the Outcome of Wnt Signalling" Biol. Chem. 383:255-261 ( 2002).
Chen et al., "Cloning and identification of a cDNA that encodes a novel human protein with thrombospondin type I repeat domain, hPWTSR" Molecular Biology Reports 29:287-291 ( 2002).
Giles et al., "Caught up in a Wnt storm:Wnt signaling in cancer" Biochimica et Biophysica Acta 1653:1-24 ( 2003).
Kamata et al., "R-spondin, a novel gene with thrombospondin type 1 domain, was expressed in the dorsal nueral tube and affected in Wnts mutants" Biochimica et Biophysica Acta 1676:51-62 ( 2004).

(Continued)

*Primary Examiner* — Maria Marvich
(74) *Attorney, Agent, or Firm* — Stephanie Yonker

(57) ABSTRACT

The present invention relates to a composition useful for the diagnosis of diseases associated with aberrant expression of the genes encoding the secreted proteins Futrin 1, 2, 3 and/or 4(=R-Spondin 2, 3, 1 and 4, respectively), e.g. in connection with tumors or diseases of the muscle, kidneys or bones. The present invention also relates to a pharmaceutical composition containing a compound which is capable of modifying (a) the expression of the gene encoding Futrin 1, 2, 3 and/or 4 or (b) the activity of the Futrin 1, 2, 3 and/or 4 protein.

14 Claims, 29 Drawing Sheets

(56) References Cited

OTHER PUBLICATIONS

Kazanskaya et al., "R-Spondin2 is a Secreted Activator of Wnt/beta-Catenin Signaling and is Required for Xenopus Myogenesis" Development Cell 7:525-534 ( 2004).

Kim et al., "Mitogenic influence of human R-Spondin1 on the intestinal epithelium" Science 309:1256 ( 2005).

Kim et al., "R-Spondin Proteins, A Novel Link to beta-catenin Activation" Cell Cycle 5(1):23-26 ( 2006).

Nam et al., "Maouse Cristin/R-spondin Family Proteins are Novel Ligands for the Frizzled 8 and LRP6 Receptors and Activate Beta-Catenin-dependent Gene Expression" Journal of Biological Chemistry 281:13247-13257 ( 2006).

Peifer and Polakis. et al., "Wnt Signaling in Oncogenesis and Embryogenesis—A Look Outside the Nucleus." Science 287:1606-1609 (Mar. 3, 2000).

Prockop et al., "One strategy for cell and gene therapy: Harnessing the power of adult stem cells to repair tissue" PNAS 100 (SUPPL 1):11917-11923 ( 2003).

van Es et al., "You Wnt some, you lose some: oncogenes in the Wnt signaling pathyway" Current Opinion in Genetics & Development 13:28-33 (2003).

FIG. 3

| FIG. 3A | FIG. 3B |
| FIG. 3C | FIG. 3D |

| hRspo2 | 39.9 | | |
| --- | --- | --- | --- |
| hRspo3 | 43.7 | 45.9 | |
| hRspo4 | 40.3 | 43.9 | 41.2 |
| | hRspo1 | hRspo2 | hRspo3 |
FIG. 6B
| mRspo2 | 40.5 | 95.5 | 44.2 | 44.8 |
| --- | --- | --- | --- | --- |
| XRspo2 | 40.8 | 83.5 | 43.8 | 42.2 |
| | hRspo1 | hRspo2 | hRspo3 | hRspo4 |
FIG. 6C
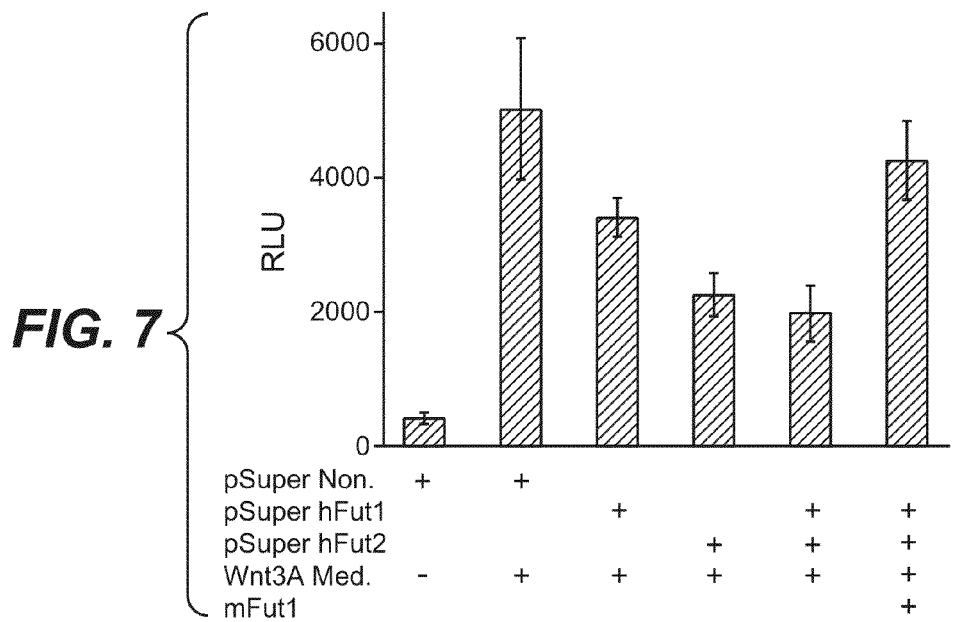
FIG. 7
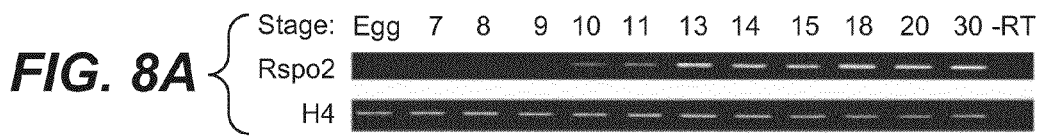
FIG. 8A

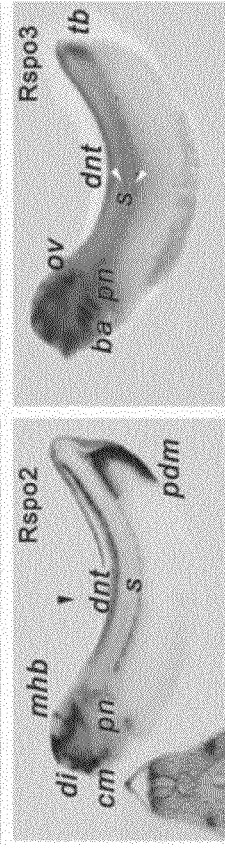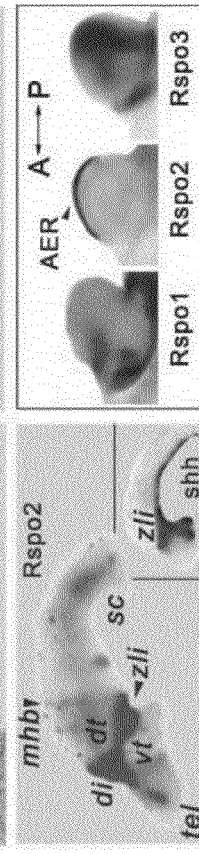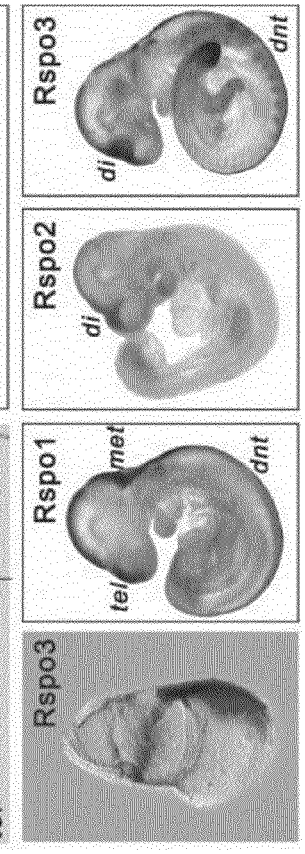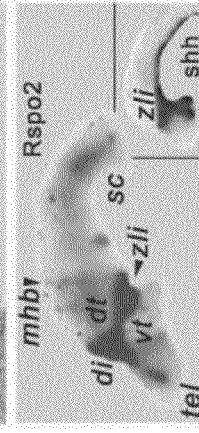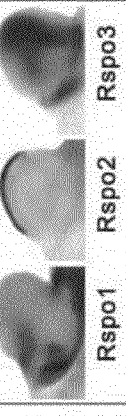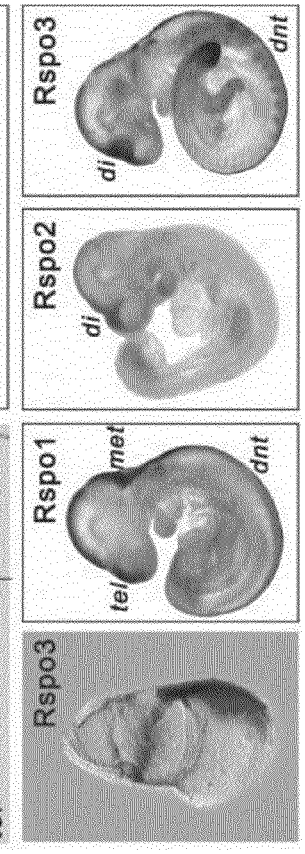

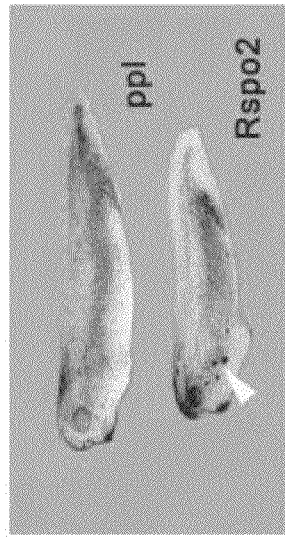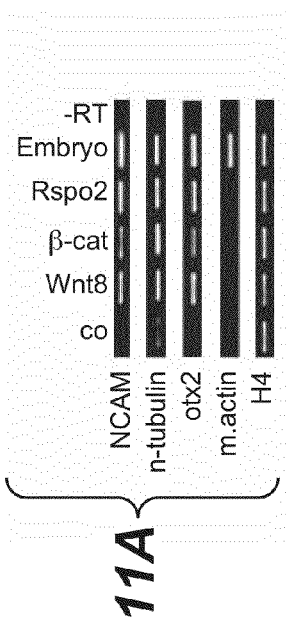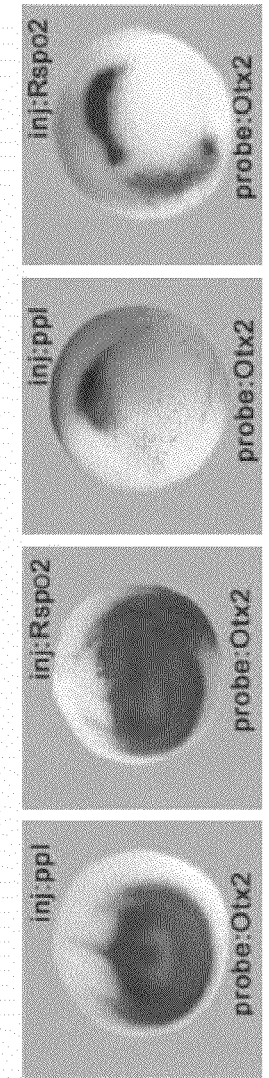

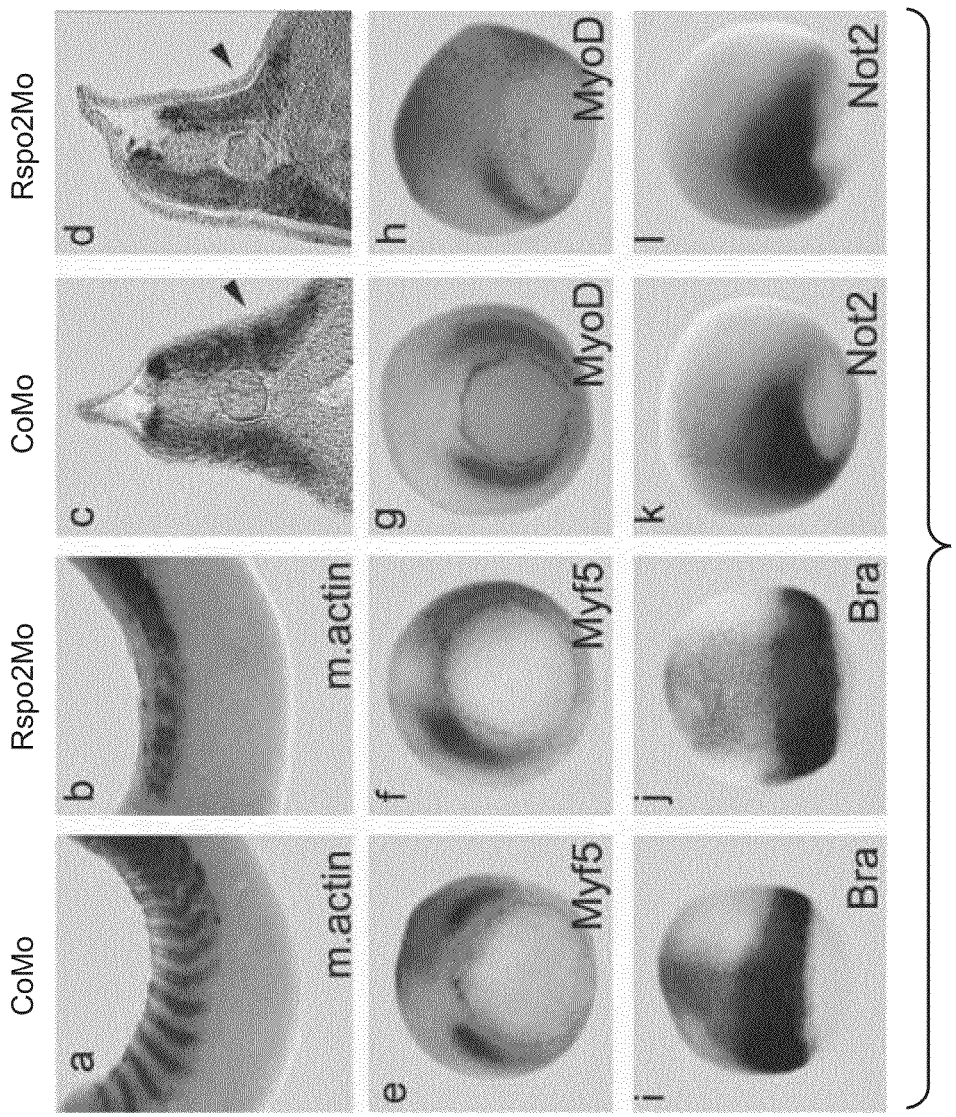
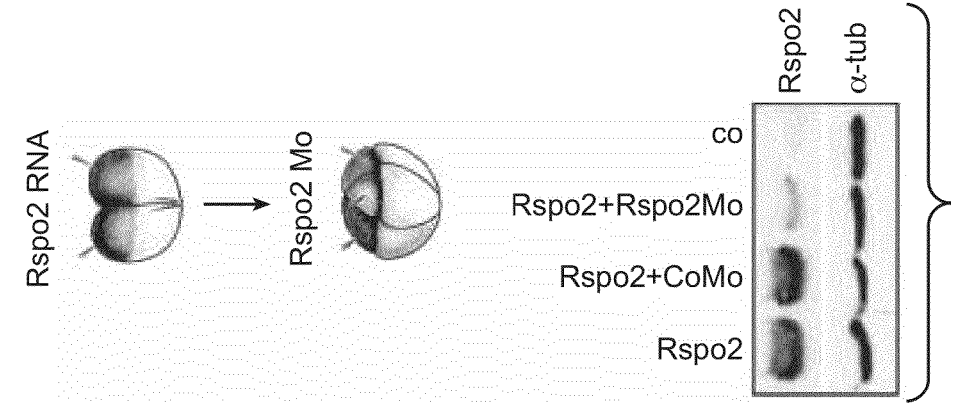

ly identified as hPWTSR (Chen et al., 29 (2002),

SEQUENCE LISTING

```
<160> NUMBER OF SEQ ID NOS: 34

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gccgtccaaa tgcagtttca ac                                              22

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```
tcccatttgc aagggttgt                                           19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agctgactgt gatacctgt                                           19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actaccgttg ttataggtg                                           19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaatgcccag aaggatttgc                                          20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggatggtgt cttttgctgg                                          20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaagcaaatt ggagtctgtc g                                        21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gattgttctc aaacccttca gg                                       22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acagacacaa gacacacacg c                                              21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgtcttctgg tggcctcag                                                 19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgagcccca gatatgaac                                                 19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgaccaactt cacatccttc c                                              21

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agggactgaa acacgggtc                                                 19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgtcttctgg tggcctcag                                                 19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aagctgggac acagcacag                                                19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaagccttgg agccttgtc                                                19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcccatttgc aagggttgt                                                19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agctgactgt gatacctgt                                                19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
actaccgttg ttataggtg                                                19

<210> SEQ ID NO 20
<211> LENGTH: 843
<212> TYPE: DNA
<213> ORGANISM: Homo sapiens

<400> SEQUENCE: 20
atgcggcttg gctgtgtgt ggtggccctg gttctgagct ggacgcacct caccatcagc    60
agccggggga tcaaggggaa aaggcagagg cggatcagtg ccgaggggag ccaggcctgt   120
gccaaaggct gtgagctctg ctctgaagtc aacggctgcc tcaagtgctc acccaagctg   180

```
ttcatcctgc tggagaggaa cgacatccgc caggtgggcg tctgcttgcc gtcctgccca      240
cctggatact tcgacgcccg caaccccgac atgaacaagt gcatcaattc ctctgcagta      300
cctgcagctc taggccaggg tcctgccctc catgtagaat gcaagatcga gcactgtgag      360
gcctgcttca gccataactt ctgcaccaag tgtaaggagg gcttgtacct gcacaagggc      420
cgctgctatc agcttgtcc cgagggctcc tcagctgcca atggcaccat ggagtgcagt       480
agtcctgcgc aatgtgaaat gagcgagtgg tctccgtggg ggccctgctc caagaagcag      540
cagctctgtg gtttccggag gggctccgag gagcggacac gcaggtgct acatgcccct       600 gtgggggacc atgctgcctg ctctgacacc aaggagaccc ggaggtgcac agtgaggaga      660
gtgccgtgtc ctgaggggca aagaggagg aagggaggcc agggccggcg ggagaatgcc       720
aacaggaacc tggccaggaa ggagagcaag gaggcgggtg ctggctctcg aagacgcaag      780
gggcagcaac agcagcagca gcaagggaca gtggggccac tcacatctgc agggcctgcc      840
tag                                                                    843

<210> SEQ ID NO 21
<211> LENGTH: 732
<212> TYPE: DNA
<213> ORGANISM: Homo sapiens

<400> SEQUENCE: 21
atgcagtttc gccttttctc ctttgccctc atcattctga actgcatgga ttacagccac       60
tgccaaggca accgatggag acgcagtaag cgagctagtt atgtatcaaa tcccatttgc      120
aagggttgtt tgtcttgttc aaaggacaat gggtgtagcc gatgtcaaca gaagttgttc      180
ttcttccttc gaagagaagg gatgcgccag tatggagagt gcctgcattc ctgcccatcc      240
gggtactatg acaccgagc cccagatatg aacagatgtg caagatgcag aatagaaaac      300
tgtgattctt gctttagcaa agacttttgt accaagtgca aagtaggctt ttatttgcat      360
agaggccgtt gctttgatga atgtccagat ggttttgcac cattagaaga aaccatggaa      420
tgtgtggaag atgtgaagt tggtcattgg agcgaatggg gaacttgtag cagaaataat      480
cgcacatgtg gatttaaatg gggtctggaa accagaacac ggcaaattgt taaaagcca       540 gtgaaagaca caataccgtg tccaaccatt gctgaatcca ggagatgcaa gatgacaatg      600
aggcattgtc caggagggaa gagaacacca aaggcgaagg agaagaggaa caagaaaaag      660
aaaaggaagc tgatagaaag ggcccaggag caacacagcg tcttcctagc tacagacaga      720
gctaaccaat aa                                                          732

<210> SEQ ID NO 22
<211> LENGTH: 819
<212> TYPE: DNA
<213> ORGANISM: Homo sapiens

<400> SEQUENCE: 22
atgcacttgc gactgatttc ttggcttttt atcattttga actttatgga atacatcggc       60
agccaaaacg cctcccgggg aaggcgccag cgaagaatgc atcctaacgt tagtcaaggc      120
tgccaaggag gctgtgcaac atgctcagat tacaatggat gtttgtcatg taagcccaga      180 ctatttttg ctctggaaag aattggcatg aagcagattg gagtatgtct ctcttcatgt      240
ccaagtggat attatggaac tcgatatcca gatataaata gtgtacaaa atgcaaagct      300 gactgtgata cctgtttcaa caaaaatttc tgcacaaaat gtaaagtgg atttacttta      360 caccttggaa agtgccttga caattgccca gaagggttgg aagccaacaa ccatactatg      420
```

```
gagtgtgtca gtattgtgca ctgtgaggtc agtgaatgga atccttggag tccatgcacg        480
aagaagggaa aaacatgtgg cttcaaaaga gggactgaaa cacgggtccg agaaataata        540
cagcatcctt cagcaaaggg taacctgtgt cccccaacaa atgagacaag aaagtgtaca        600
gtgcaaagga agaagtgtca aagggagaaa cgaggaaaaa aaggaaggga gaggaaaaga        660
aaaaaaccta ataaaggaga agtaaagaa gcaatacctg acagcaaaag tctggaatcc         720
agcaaagaaa tcccagagca acgagaaaac aaacagcagc agaagaagcg aaaagtccaa        780
gataaacaga atcggtatc agtcagcact gtacactag                                819
```

<210> SEQ ID NO 23
<211> LENGTH: 672
<212> TYPE: DNA
<213> ORGANISM: Homo sapiens

<400> SEQUENCE: 23

```
atgcgggcgc cactctgcct gctcctgctc gtcgcccacg ccgtggacat gctcgccctg         60
aaccgaagga agaagcaagt gggcactggc ctgggggggca actgcacagg ctgtatcatc       120
tgctcagagg agaacggctg ttccacctgc agcagagggc tcttcctgtt catccgccgg        180
gaaggcatcc gccagtacgg caagtgcctg cacgactgtc cccctgggta cttcggcatc        240
cgcggccagg aggtcaacag gtgcaaaaaa tgtgggggcca cttgtgagag ctgcttcagc        300
caggacttct gcatccggtg caagaggcag ttttacttgt acaaggggaa gtgtctgccc        360
acctgcccgc cgggcacttt ggcccaccag aacacgggg agtgccaggg ggagtgtgaa         420
ctgggtccct ggggcggctg gagcccctgc acacacaatg aaagacctg cggctcggct         480 tggggcctgg agagccgggt acgagaggct ggccgggctg gcatgaggga gcagccacc        540 tgccaggtgc tttctgagtc aaggaaatgt cccatccaga ggccctgccc aggagagagg        600
agccccggcc agaagaaggg caggaaggac cggcgcccac gcaaggacag gaagctggac        660
cgcaggctgg ac                                                            672
```

<210> SEQ ID NO 24
<211> LENGTH: 732
<212> TYPE: DNA
<213> ORGANISM: Xenopus laevis

<400> SEQUENCE: 24

```
atgcagtttc aactcttttc attcgccctg atcatcctga actgtgtgga ttacagtcac         60
tgccaagcct cccgctggag acggagcaag agagccagct atgggaccaa cccgatatgc       120
aaaggttgcc tgtcctgctc aaaagataat gggtgcctcc gctgccagcc aaaactgttt        180
ttctttctgc gaagagaagg tatgaggcag tatggagagt gtctgcagtc ctgccctccg        240
ggatactatg gagtcagagg acctgatatg aacaggtgtt ccagatgcag aattgaaaat        300
tgcgactctt gttttagtag agatttttgc ataaagtgca atcgggcttt ttactccctc        360
aaggggcaat gctttgaaga atgcccagaa ggatttgcac cactggatga taccatggtg        420
tgtgtggatg gctgcgaagt agggccatgg agtgaatggg gcacatgcag ccgaaataac        480
agaacgtgcg gtttcaaatg gggcctggag accagaacgc gacaaattgt gaagaaacca        540
gcaaaagaca ccatccccctg cccaactatt gctgaatcca agatgtaa gatggcaata        600 agacactgcc ctggaggaaa gagaactaca agaagaagg acaagaggaa caagaagaag        660
aaaaagaagt tactggagag ggcccaagag cagcacagcg tcgtccttgc tacagaccgg        720
```
tctagccaat ag                                                    732

<210> SEQ ID NO 25
<211> LENGTH: 262
<212> TYPE: PRT
<213> ORGANISM: Homo sapiens

<400> SEQUENCE: 25

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Cys
                85                  90                  95

Lys Ile Glu His Cys Glu Ala Cys Phe Ser His Asn Phe Cys Thr Lys
            100                 105                 110

Cys Lys Glu Gly Leu Tyr Leu His Lys Gly Arg Cys Tyr Pro Ala Cys
        115                 120                 125

Pro Glu Gly Ser Ser Ala Ala Asn Gly Thr Met Glu Cys Ser Ser Pro
    130                 135                 140

Ala Gln Cys Glu Met Ser Glu Trp Ser Pro Trp Gly Pro Cys Ser Lys
145                 150                 155                 160

Lys Gln Gln Leu Cys Gly Phe Arg Arg Gly Ser Glu Glu Arg Thr Arg
                165                 170                 175

Arg Val Leu His Ala Pro Val Gly Asp His Ala Ala Cys Ser Asp Thr
            180                 185                 190

Lys Glu Thr Arg Arg Cys Thr Val Arg Arg Val Pro Cys Pro Glu Gly
        195                 200                 205

Gln Lys Arg Arg Lys Gly Gly Gln Gly Arg Arg Glu Asn Ala Asn Arg
    210                 215                 220

Asn Leu Ala Arg Lys Glu Ser Lys Glu Ala Gly Ala Gly Ser Arg Arg
225                 230                 235                 240

Arg Lys Gly Gln Gln Gln Gln Gln Gln Gly Thr Val Gly Pro Leu
                245                 250                 255

Thr Ser Ala Gly Pro Ala
            260

<210> SEQ ID NO 26
<211> LENGTH: 243
<212> TYPE: PRT
<213> ORGANISM: Homo sapiens

<400> SEQUENCE: 26

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg

```
                    50                  55                  60
Arg Glu Gly Met Arg Gln Tyr Gly Glu Cys Leu His Ser Cys Pro Ser
 65                  70                  75                  80

Gly Tyr Tyr Gly His Arg Ala Pro Asp Met Asn Arg Cys Ala Arg Cys
                     85                  90                  95

Arg Ile Glu Asn Cys Asp Ser Cys Phe Ser Lys Asp Phe Cys Thr Lys
                100                 105                 110

Cys Lys Val Gly Phe Tyr Leu His Arg Gly Arg Ser Phe Asp Glu Cys
            115                 120                 125

Pro Asp Gly Phe Ala Pro Leu Glu Glu Thr Met Glu Cys Val Glu Gly
        130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
210                 215                 220

Ile Glu Arg Ala Gln Glu Gly His Ser Val Phe Leu Ala Thr Asp Arg
225                 230                 235                 240

Ala Asn Gln
```

<210> SEQ ID NO 27
<211> LENGTH: 272
<212> TYPE: PRT
<213> ORGANISM: Homo sapiens

<400> SEQUENCE: 27

```
Met His Leu Arg Leu Ile Ser Trp Leu Phe Ile Ile Leu Asn Phe Met
 1                   5                  10                  15

Glu Tyr Ile Gly Ser Gln Asn Ala Ser Arg Gly Arg Gln Arg Arg
                 20                  25                  30

Met His Pro Asn Val Ser Gln Gly Cys Gln Gly Gly Cys Ala Thr Cys
                 35                  40                  45

Ser Asp Tyr Asn Gly Cys Leu Ser Cys Lys Pro Arg Leu Phe Phe Ala
         50                  55                  60

Leu Glu Arg Ile Gly Met Lys Gln Ile Gly Val Cys Leu Ser Ser Cys
 65                  70                  75                  80

Pro Ser Gly Tyr Tyr Gly Thr Arg Tyr Pro Asp Ile Asn Lys Cys Thr
                 85                  90                  95

Lys Cys Lys Ala Asp Cys Asp Thr Cys Phe Asn Lys Asn Phe Cys Thr
                100                 105                 110

Lys Cys Lys Ser Gly Phe Tyr Leu His Leu Gly Lys Cys Leu Asp Asn
            115                 120                 125

Cys Pro Glu Gly Leu Glu Ala Asn Asn His Thr Met Glu Cys Val Ser
        130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
```

```
                180             185             190
Thr Asn Glu Thr Arg Lys Cys Thr Val Gln Arg Lys Cys Gln Lys
            195                 200                 205

Gly Glu Arg Gly Lys Lys Gly Arg Glu Arg Lys Arg Lys Pro Asn
            210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
            245                 250                 255

Arg Lys Val Gln Asp Lys Gln Lys Ser Val Ser Val Ser Thr Val His
            260                 265                 270

<210> SEQ ID NO 28
<211> LENGTH: 224
<212> TYPE: PRT
<213> ORGANISM: Homo sapiens

<400> SEQUENCE: 28

Met Arg Ala Pro Leu Cys Leu Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
        35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
        115                 120                 125

His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gly Gln Lys Lys Gly Arg
        195                 200                 205

Lys Asp Arg Arg Pro Arg Lys Asp Arg Lys Leu Asp Arg Arg Leu Asp
    210                 215                 220

<210> SEQ ID NO 29
<211> LENGTH: 262
<212> TYPE: PRT
<213> ORGANISM: Homo sapiens

<400> SEQUENCE: 29

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
```

```
                    20                  25                  30
        Ser Ala Glu Gly Ser Gln Ala Cys Ala Lys Gly Cys Glu Leu Cys Ser
                35                  40                  45

Glu Val Asn Gly Cys Leu Lys Cys Ser Pro Lys Leu Phe Ile Leu Leu
         50                  55                  60

Glu Arg Asn Asp Ile Arg Gln Val Gly Val Cys Leu Pro Ser Cys Pro
         65                  70                  75                  80

Pro Gly Tyr Phe Asp Ala Arg Asn Pro Asp Met Asn Lys Cys Ile Cys
                        85                  90                  95

Lys Ile Glu His Cys Glu Ala Cys Phe Ser His Asn Phe Cys Thr Lys
                    100                 105                 110

Cys Lys Glu Gly Leu Tyr Leu His Lys Gly Arg Cys Tyr Pro Ala Cys
                    115                 120                 125

Pro Glu Gly Ser Ser Ala Ala Asn Gly Thr Met Glu Cys Ser Ser Pro
                130                 135                 140

Ala Gln Cys Glu Met Ser Glu Trp Ser Pro Trp Gly Pro Cys Ser Lys
        145                 150                 155                 160

Lys Gln Gln Leu Cys Gly Phe Arg Arg Gly Ser Glu Glu Arg Thr Arg
                        165                 170                 175

Arg Val Leu His Ala Pro Val Gly Asp His Ala Ala Cys Ser Asp Thr
                    180                 185                 190

Lys Glu Thr Arg Arg Cys Thr Val Arg Arg Val Pro Cys Pro Glu Gly
                    195                 200                 205

Gln Lys Arg Arg Lys Gly Gly Gln Gly Arg Arg Glu Asn Ala Asn Arg
                210                 215                 220

Asn Leu Ala Arg Lys Glu Ser Lys Glu Ala Gly Ala Gly Ser Arg Arg
        225                 230                 235                 240

Arg Lys Gly Gln Gln Gln Gln Gln Gln Gly Thr Val Gly Pro Leu
                        245                 250                 255

Thr Ser Ala Gly Pro Ala
                    260

<210> SEQ ID NO 30
<211> LENGTH: 243
<212> TYPE: PRT
<213> ORGANISM: Homo sapiens

<400> SEQUENCE: 30

Met Gln Phe Arg Leu Phe Ser Phe Ala Leu Ile Ile Leu Asn Cys Met
        1               5                   10                  15

Asp Tyr Ser His Cys Gln Gly Asn Arg Trp Arg Ser Lys Arg Ala
                    20                  25                  30

Ser Tyr Val Ser Asn Pro Ile Cys Lys Gly Cys Leu Ser Cys Ser Lys
                        35                  40                  45

Asp Asn Gly Cys Ser Arg Cys Gln Gln Lys Leu Phe Phe Phe Leu Arg
         50                  55                  60

Arg Glu Gly Met Arg Gln Tyr Gly Glu Cys Leu His Ser Cys Pro Ser
         65                  70                  75                  80

Gly Tyr Tyr Gly His Arg Ala Pro Asp Met Asn Arg Cys Ala Arg Cys
                        85                  90                  95

Arg Ile Glu Asn Cys Asp Ser Cys Phe Ser Lys Asp Phe Cys Thr Lys
                    100                 105                 110

Cys Lys Val Gly Phe Tyr Leu His Arg Gly Arg Ser Phe Asp Glu Cys
                    115                 120                 125
```

```
Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
210                 215                 220

Ile Glu Arg Ala Gln Glu Gly His Ser Val Phe Leu Ala Thr Asp Arg
225                 230                 235                 240

Ala Asn Gln
```

<210> SEQ ID NO 31
<211> LENGTH: 272
<212> TYPE: PRT
<213> ORGANISM: Homo sapiens

<400> SEQUENCE: 31

```
Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
                20                  25                  30

Met His Pro Asn Val Ser Gln Gly Cys Gln Gly Gly Cys Ala Thr Cys
            35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Pro Asn
210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255
```

```
Arg Lys Val Gln Asp Lys Gln Lys Ser Val Ser Val Thr Val His
            260                 265                 270

<210> SEQ ID NO 32
<211> LENGTH: 224
<212> TYPE: PRT
<213> ORGANISM: Homo sapiens

<400> SEQUENCE: 32

Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
        115                 120                 125

His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gly Gln Lys Lys Gly Arg
        195                 200                 205

Lys Asp Arg Arg Pro Arg Lys Asp Arg Lys Leu Asp Arg Leu Asp
    210                 215                 220

<210> SEQ ID NO 33
<211> LENGTH: 820
<212> TYPE: DNA
<213> ORGANISM: Homo sapiens

<400> SEQUENCE: 33
atgcacttgc gactgatttc ttggcttttt atcattttga actttatgga atacatcggc      60
agccaaaacg cctcccgggg aaggcgccag cgaagaatgc atcctaacgt tagtcaaggc     120
tgccaaggag gctgtgcaac atgctcagat tacaatggat gtttgtcatg taagcccaga     180
ctattttttg ctctggaaag aattggcatg aagcagattg agtatgtctc tcttcatgt      240 ccaagtggat attatggaac tcgatatcca gatataaata agtgtacaaa atgcaaagct     300
gaactgtgat acctgtttca acaaaaattt ctgcacaaaa tgtaaaagtg gattttactt     360
acaccttgga aagtgccttg caattgccc agaagggttg gaagccaaca accatactat     420
ggagtgtgtc agtattgtgc actgtgaggt cagtgaatgg aatccttgga gtccatgcac      480
gaagaaggga aaaacatgtg gcttcaaaag agggactgaa cacgggtcc gagaaataat     540
```

```
acagcatcct tcagcaaagg gtaacctgtg tcccccaaca aatgagacaa gaaagtgtac    600
agtgcaaagg aagaagtgtc agaagggaga acgaggaaaa aaaggaaggg agaggaaaag    660
aaaaaaacct aataaggag aaagtaaaga agcaatacct gacagcaaaa gtctggaatc     720
cagcaaagaa atcccagagc aacgagaaaa caaacagcag cagaagaagc gaaaagtcca    780
agataaacag aaatcggtat cagtcagcac tgtacactag                          820
```

<210> SEQ ID NO 34
<211> LENGTH: 280
<212> TYPE: PRT
<213> ORGANISM: Homo sapiens
<400> SEQUENCE: 34

```
Met Arg Leu Gly Leu Cys Val Val Ala Leu Val Leu Ser Trp Thr His
1               5                   10                  15

Leu Thr Ile Ser Ser Arg Gly Ile Lys Gly Arg Gln Arg Arg Ile
            20                  25                  30

Ser Ala Glu Gly Ser Gln Ala Cys Ala Lys Gly Cys Glu Leu Cys Ser
            35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Asn
                85                  90                  95

Ser Ser Ala Val Pro Ala Ala Leu Gly Gln Gly Pro Ala Leu His Val
            100                 105                 110

Glu Cys Lys Ile Glu His Cys Glu Ala Cys Phe Ser His Asn Phe Cys
        115                 120                 125

Thr Lys Cys Lys Glu Gly Leu Tyr Leu His Lys Gly Arg Cys Tyr Pro
    130                 135                 140

Ala Cys Pro Glu Gly Ser Ser Ala Ala Asn Gly Thr Met Glu Cys Ser
145                 150                 155                 160

Ser Pro Ala Gln Cys Glu Met Ser Glu Trp Ser Pro Trp Gly Pro Cys
                165                 170                 175

Ser Lys Lys Gln Gln Leu Cys Gly Phe Arg Arg Gly Ser Glu Glu Arg
            180                 185                 190

Thr Arg Arg Val Leu His Ala Pro Val Gly Asp His Ala Ala Cys Ser
        195                 200                 205

Asp Thr Lys Glu Thr Arg Arg Cys Thr Val Arg Arg Val Pro Cys Pro
    210                 215                 220

Glu Gly Gln Lys Arg Arg Lys Gly Gly Gln Gly Arg Arg Glu Asn Ala
225                 230                 235                 240

Asn Arg Asn Leu Ala Arg Lys Glu Ser Lys Glu Ala Gly Ala Gly Ser
                245                 250                 255

Arg Arg Arg Lys Gly Gln Gln Gln Gln Gln Gln Gly Thr Val Gly
            260                 265                 270

Pro Leu Thr Ser Ala Gly Pro Ala
    275                 280
```

COMPOSITIONS FOR DIAGNOSIS AND THERAPY OF DISEASES ASSOCIATED WITH ABERRANT EXPRESSION OF FUTRINS (R-SPONDINS) AND/OR WNT

CROSS-REFERENCE TO RELATED APPLICATIONS

This application is a continuation of U.S. application Ser. No. 13/951,152, filed Jul. 25, 2013 which is a divisional of U.S. application Ser. No. 13/931,481, filed Jun. 28, 2013, which is a divisional of U.S. application Ser. No. 10/575,217, filed Apr. 10, 2006, the contents of both of which are hereby incorporated by reference, which is a national stage application of International Application No. PCT/EP2004/011269 having an international filing date of Oct. 8, 2004 and which claims benefit under 35 U.S.C. §119 to European Patent Application No. 0302300.7 filed Oct. 10, 2003.

SEQUENCE LISTING

The instant application contains a Sequence Listing which has been submitted in ASCII format via EFS-Web and is hereby incorporated by reference in its entirety. Said ASCII copy, created on Apr. 3, 2014, is named P5660D3C1_Sequence_Listing.txt and is 31,571 bytes in size.

BACKGROUND

The present invention relates to compositions useful for the diagnosis and therapy of diseases associated with aberrant expression of the genes encoding the proteins Futrin 1, 2, 3 and/or 4 (=R-Spondin 2, 3, 1 and 4, respectively). These diseases include tumors of e.g. the breast, ovary, liver, uterus, cervix, colon, lung, ovary, rectum, testis, pancreas, bones and skin, as well as diseases involving muscle, bone, lipid and glucose metabolism, and obesity. The present invention also relates to a pharmaceutical composition containing a compound which is capable of modifying (a) the expression of the gene encoding Futrin 1, 2, 3 and/or 4 or (b) the activity of Futrin 1, 2, 3 and/or 4.

The Wnt signal cascade plays a crucial role as regards regulation of survival, proliferation and differentiation of cells during embryogenesis, and in the adult as shown, e.g., in *Drosophila*, *Xenopus* and mice (Nusse and Varmus, Cell 69 (1992), 1073-1087). Wnt-genes encode secretory glycoproteins which activate a well characterized signal cascade via a Wnt receptor called "frizzled".

The Wnt signalling cascade and its components also play an important role in various diseases which makes it desirable to modulate its activity:

i) Cancer

Tumorigenesis represents a complex multistage process in which genetic changes and environmental factors are thought to deregulate the cellular processes that control cell proliferation and differentiation. Several studies indicate that an aberrant Wnt signal cascade is involved in the development of colon cancer, breast cancer and melanoma (Pfeifer, Science, 2 75 (1997), 1752-1753; Polakis, Genes Dev. 14 (2000), 1837-1851). The first gene encoding a protein of the Wnt signal cascade, int-1, was isolated from mouse mammary tumor virus (MMTV) and it could be shown that it is an oncogene. It is thus well established that an aberrant regulation of the activity of Wnt and/or components of the Wnt signal cascade downstream of the Wnt signal, e.g., beta-catenin and APC, are involved in tumorigenesis.

ii) Bone Disease

Wnt signals promote bone formation (e.g. Yang, Development, 130(2003), 1003-15; Fischer, J. Biol. Chem. 277 (2002) 30870-30878). Consistent with this notion, a gain-of-function mutation of the Wnt receptor LRP5 causes high bone disease (Boyden, et al., 346 (2002) N Engl J Med, 1513-21; Little, et al., 70 (2002) Am J Hum Genet, 11-9). Conversely, inactivating mutations in LRP5 leads to osteoporosis-pseudoglioma syndrome in humans (Kato, et al., 157 (2002) J Cell Biol, 303-14; Gong, et al., 107 (2001) Cell, 513-23).

iii) Eye Disease

Inactivating mutation in the Wnt receptor LRP5 lead to pseudoglioma in humans and eye malformations in mice (Kato, et al., 157 (2002) J Cell Biol 303-314; Gong, et al., 107 (2001) Cell, 513-523).

iv) Kidney

Aberrant Wnt signalling is involved in renal fibrosis (Surendran, Am J Physiol Renal Physiol 282 (2002) 431-441) and polycystic kidney disease (Saadi-Kheddouci, Oncogene 20 (2001) 5972-5981).

v) Lipid and Glucose Metabolism, Obesity

Deficiency of the Wnt receptor LRP5 in mice leads to increased plasma cholesterol levels in mice fed a high-fat diet, because of the decreased hepatic clearance of chylomicron remnants. In addition, when fed a normal diet, LRP5-deficient mice show a markedly impaired glucose tolerance (Fujino, et al., 100 (2003) Proc Natl Acad Sci USA, 229-234.) Administration of the LRP5 antagonist Dkk1 to mice reduces glucose uptake in various cell line and decreases fat deposition (WO 02/066509).

It is thus clear from the above that the Wnt signalling pathway is involved in a variety of human diseases. Yet, means for the therapy or diagnosis of diseases associated with a dis-regulated Wnt signal cascade are insufficiently available. Thus, the use of reliable diagnostic molecular markers would be helpful for an understanding of the molecular basis of diseases associated with an aberrant Wnt signal cascade. It can be expected that such markers are also useful for therapy and for the development of novel therapeutic avenues for treatment of Wnt signal cascade dependent diseases, as detailed above.

Thus, the technical problem underlying the present invention is to provide means for diagnosis and therapy of diseases associated with an aberrant Wnt signal cascade.

The solution to said technical problem is achieved by providing the embodiments characterized in the claims.

During the experiments resulting in the present invention four genes, futrin 1, 2, 3 and 4, could be identified the products of which are modulators of the Wnt pathway. Futrin 2 was previously identified as hPWTSR (Chen et al., 29 (2002), Mol. Biol. Rep. 287-292), a protein of before unknown role or function, expressed in numerous cell types. Further, human Futrin 1, 2, 3, and 4 were described as Stem Cell Growth Factor-Like Polypeptides, which are able to promote proliferation of hematopoietic stem cells (WO-A-01/77169; WO-A-01/07611).

SUMMARY

In the present invention the following is shown for the first time: 1) Futrins enhance Wnt signalling and this is of physiological relevance since inhibition of Futrin 1 or 2 results in inhibition of the Wnt signal cascade (Wnt/(β-catenin signalling). These data show that Futrins can be regarded as Wnt modulators. Futrin 1 (Rspo2) is coexpressed with and positively regulated by Wnt signals and synergizes with Wnt to activate β-catenin. Analysis of functional interaction with components of the Wnt/β-catenin pathway suggests that Rspo2 functions extracellularly at the level of receptor ligand interaction. Antisense Morpholino experiments in *Xenopus* embryos and RNAi experiments in HeLa cells revealed that Rspo2 is required for Wnt/β-catenin signalling. In *Xenopus* embryos depleted of Rspo2 the muscle markers myoD and myf5 fail to be activated and later muscle development is impaired. The results indicate that Rspo2 is a novel activator of the Wnt/β-catenin cascade. Thus, Futrins like Rspo2 (Futrin 1) are useful for the diagnosis and the development of therapies for Wnt-LRP mediated diseases, including but not limited to tumor suppression, bone formation, cholesterol and glucose metabolism (including diabetes), obesity, kidney disease and eye disease. 2.) Since the data obtained show that Futrin 1 is required for muscle formation Futrin 1 is useful for the diagnosis and the development of therapies for muscle related diseases, including muscle regeneration. 3.) The data show that Futrins are aberrantly expressed in a variety of human tumors. Thus, Futrins are useful for tumor diagnosis and the development of cancer therapies. For example it has been found out that in most of the tumors the expression of Futrins 1-3 is dramatically decreased (colon, stomach, lung, rectum tumors for Futrin 1, breast, ovary, bladder, uterus, cervix, rectum tumors for Futrin 2, uterus and cervix tumors for Futrin 3). In a few cases the expression of Futrins 1-3 is upregulated (one case of stomach tumor for Futrin 1 and 2, ovary tumor for Futrin 3). Futrin 4 shows very low level of expression in most of the tissues studied, except ovary.

Thus, the inhibition of the Wnt signal cascade by inhibiting the expression/activity of Futrins or by stimulating the expression/activity of the Futrins will have a therapeutic effect. Likewise, the activation of the Wnt signal cascade by decreasing the expression of Futrin and/or by repressing the activity of the polypeptide itself will have a therapeutic effect.

BRIEF DESCRIPTION OF THE DRAWINGS

(FIG. 2A) Identification of *Xenopus* Rspo2 by expression screening. An expression screen was carried out in 293T cells transfected with a Wnt-responsive reporter (TOP-FLASH) and plasmid DNA pools from a *Xenopus* eye cDNA library. RLU: relative light units. (FIG. 2B) The C-terminus of Rspo2 mediates cell surface retention. Myc-tagged Rspo2 (wt) or Rspo2ΔC (ΔC) were transfected in 293T cells, and cell lysate and medium were analysed by Western blot. Co, untransfected cells. (FIG. 2C) Rspo2 activates Wnt/β-catenin signalling. TOPFLASH luciferase reporter assays were carried out in 293T cells with the following transfected DNAs: mouse Wnt1 (Wnt), 5 ng; mouse frizzled8(fz), 1 ng; *Xenopus* Rspo2 (Rspo2), 0.1, 0.3, 0.9 and 2.7 ng. (FIG. 2D) Rspo2 enhances Wnt3a signalling. Mouse Wnt3a, *Xenopus* Rspo2ΔC (Rspo2ΔC) or mock-conditioned media were added to 293T cells followed by TOPFLASH luciferase reporter assays. (FIG. 2E) Rspo2 stabilizes β-catenin. (top) 293T cells were treated with Rspo2ΔC, Wnt3a or mock-conditioned media for 1 or 4 hours as indicated. Cytosolic fractions were subjected to Western blot and probed for β-catenin and α-tubulin (loading control). (bottom) immuno-histochemical staining of β-catenin in SHEP cells after 3 hour treatment with the conditioned media indicated. Arrowheads indicate nuclear β-catenin. The percentage of cells showing the represented staining is 90% (Co), 85% (Rspo2), 80% (Wnt3a) and 90% (Wnt3a+Rspo2). (FIG. 2F) Domain analysis of Rspo2. (top) schematic drawing of *Xenopus* Rspo2 and deletion constructs, sp, signal peptide; FU1, 2, furin-like domains; TSP1, thrombospondin type 1 domain; C, positively charged C-terminus. (bottom). TOPFLASH luciferase reporter assays were carried out in 293T cells with the indieated constructs. Equal protein production was confirmed by Western blot (data not shown).

FIG. 3A-D: Multisequence nucleic acid alignment of cDNAs encoding human Futrin 1 (SEQ ID NO:21) Futrin 2 (SEQ ID NO:33), Futrin 3 (SEQ ID NO:20) and Futrin 4 (SEQ ID NO:23) and *Xenopus* Futrin 1 (SEQ ID NO:24). Identical nucleotides are highlighted in grey. All nucleic acid sequences begin with the translation initiator ATG codon indicated with an asterisk.

FIG. 4: Multisequence amino acid alignment of human Futrin 1 (SEQ ID NO:26), Futrin 2 (SEQ ID NO:27), Futrin 3 (SEQ ID NO:34) and Futrin 4 (SEQ ID NO:28) deduced from human cDNAs (see FIG. 3). Identical amino acids are highlighted in grey, similar amino acids are in dotted box.

(FIG. 5A) Wnt-responsive luciferase reporter assays were performed in 96 well plates in triplicates as described (Wu et al., Curr Biol 10 (2000), 1611-1614). Luciferase activity was normalized against Renilla activity using a commercial kit (Clonetech). (FIG. 5B) Wnt1=mouse Wnt1, fz8=mouse frizzled8, Futrin1=*xenopus* Futrin 1, Wnt3A=mouse Wnt3A, (0.1 ng) in A indicates amount of plasmid DNA transfected per well, RLU: relative luciferase units.

FIG. 6A-C: Sequence comparison of human Rspo proteins (hR-spondin 1 to 4). (FIG. 6A) Alignment of human (h) Rspo proteins (SEQ ID NOS:29-32, respectively, in order of appearance) (corresponding to the alignments of human Fut1-4 in FIG. 4 except that different designations are used). The signal peptide, furin-like domains and thrombospondin type 1 domain are underlined and conserved amino acids are shown in grey. (FIG. 6B, FIG. 6C) Rspo homology matrix showing overview of amino acid identity in % between human Rspo proteins (FIG. 6B) and between *Xenopus* (X) or mouse (m) Rspo2 and human Rspo proteins, respectively (FIG. 6C).

FIG. 7: Human Futrin 1 and 2 are required for Wnt signaling. Hela cells were transfected in 24-well plates with the Wnt reporter 7LEF-Rev-fosLuc, pRL-TK and pSuper plasmids that produce either siRNA against human Futrin1 and 2 or a nonsense control. Three days after transfection, mouse Wnt3A conditioned medium was added to the culture to stimulate Wnt signalling. 24 hours later, luciferase activity was determined.

FIG. 8A-M: Expression analysis of *Xenopus* and mouse R-spondins, (FIG. 8A) Rspo2 expression during *Xenopus* development at the indieated embryonic stages analysed by RT-PCR. Histone H4 was used for normalization. –RT, minus reverse transcription control. (FIG. 8B-H) *Xenopus* whole mount in situ hybridizations of the indicated genes. (FIG. 8B) Stage 11 embryo, dorso-vegetal view; dbl, dorsal blastoporal lip. (FIG. 8C) Stage 12 embryo, dorsal view with anterior up. An anterior neural expression domain is indicated by arrowhead. (FIG. 8D) Stage 15 embryo, dorsal view with anterior up. (FIG. 8E) Stage 14 embryo, dorsal view with anterior up. (FIG. 8F-G) Tailbud stage embryos; ba, branchial arches; cm, cranial musculature; di, diencephalon; dnt, dorsal neural tube; mhb, midbrain-hindbrain boundary; ov, otic vesicle; pn, pronephros; pdm, proctodeum; s, somites; tb, tailbud mesoder. Inset in (F) shows a transverse section at the level indicated by arrowhead, showing expression in dorsal neural tube and in the dorsal- and ventral-most parts of the somites. (FIG. 8H) Dissected *Xenopus* tadpole brain (lateral view) showing expression in diencephalons (di) and zona limitans intrathala ica (zli), where sonic hedgehog is expressed (inset). dt, vt, dorsal and ventral thalamus, respectively, sc, spinal cord; tel, telencephalon; (FIG. 8I-M) Mouse whole mount in situ hybridizations of the indicated genes. (FIG. 8I) limb buds of day 12.5 mouse embryos. AER, apical ectodermal ridge. (FIG. 8J) Day 7.5 mouse embryo showing Rspo3 expression in the primitive streak. (FIG. 8K-M) Day 9.5 mouse embryos. di, diencephalon; dnt, dorsal neural tube; inet, metencephalon; tel, telencephalon.

(FIG. 9A) Comparison of XRspo2, XWnt8 and XWnt3a expression pattern in early neurula embryos by whole mount in situ hybridization. Dorsal view, anterior up. (FIG. 9B) (top) Diagram of experiment. Four cell stage embryos were injected with 50 pg pCS-ppl (preprolactin), pCSXWnt8 or pCS-β-catenin into each blastomere, DMZs were dissected, cultured until stage 11 equivalent and analyzed by RT-PCR. (Bottom) RT-PCR analysis of the indicated genes. −RT, minus reverse transcription control. (FIG. 9C-E) Four cell stage embryos were injected with 50 pg pCS-Wnt8, pCS-Wizt3a or pCS-ppl into one blastomere and fixed at stage 11 for in situ hybridisation with XRspo2.

FIG. 10AA-FIG. 10AL. Depletion of Futrin 1 protein causes downregulation of early muscle markers and muscle defects. (FIG. 10AA, FIG. 10AC, FIG. 10AE, FIG. 10AG, FIG. 10AI, FIG. 10AK) Embryos injected with control morpholino oligo (5 ng), with Fut1-Mo (5 ng). Oligos were mixed with lineage tracer mRNA (LacZ) (blue staining) in (FIG. 10AC, FIG. 10AD, FIG. 10AE, FIG. 10AF, FIG. 10AG, FIG. 10AH) or preprolactin (ppl) RNA, visualised by in situ hybridisation (red staining) (FIG. 10AA, FIG. 10AB, FIG. 10AJ, FIG. 10AK, FIG. 10AL). In situ hybridization with probes to Xmyf5 (FIG. 10AA, FIG. 10AB), XmyoD (FIG. 10AC, FIG. 10AD), Xbra (FIG. 10AE, FIG. 10AF), Xnot (FIG. 10AG, FIG. 10AH) and muscle actin (FIG. 10AI-L) (magenta staining). Embryos in FIG. 10AK and FIG. 10AL are cut transversally. Note reduction of muscle in FIG. 10AL (right side). FIG. 10B. Fut1-Mo act specifically to inhibit translation of their cognate DNA constructs when overexpressed in embryos. mRNA (C-terminal myc tagged fut1) was injected equatorially in both blastomeres at 2-cell stage embryos. The same embryos were then injected at the 8-cell stage with 5 ng of Fut1-Mo (lane3) or control morpholino (lane2) in all vegetal blastomeres and harvested at stage 11. Tagged Futrinb protein was then visualised with a-myc antibody. FIG. 10C. Rescue of muscle marker reduction caused by Fut1-Mo by coinjection of XFut1 mRNA containing point mutations in the 5'region corresponding to morpholino oligo. Embryos were coinjected with 5 ng of Fut1-Mo (1, 2) with 50 pg of ppl or XFut1 mRNA radially in one blastomere at 4-cell stage. Expression of MyoD (1, 3) and Myf5 (2, 4) were analysed by in situ hybridization. All embryos were grouped into 3 classes (examples for MyoD are shown on the bottom of the figure): embryos with expression level on the injected side from 1-30% (class A); 30-70% (class B), and 70-100% (class C) from normal level. Bars represent the percentage of the embryos corresponding to type A, B or C. (n for Fut-Mo+ppl: 57 embryos for MyoD, 45 embryos for Myf5; n for Fut-Mo+ mRNA Ffut1: 39 embryos for MyoD and 41 embryo for Myf5).

FIG. 11A-N: Rspo2 promotes neural and muscle differentiation in *Xenopus*. (FIG. 11A) Four-cell stage embryos were injected animally with 100 pg Rspo2, 100 pg Xwnt8, or 200 pg β-catenin mRNA in each blastomere. At stage 8, animal caps were dissected, cultured until stage 18 equivalent and analyzed for expression of the indicated marker genes, −RT, minus reverse transcription control. (FIG. 11B) Two-cell stage embryos were injected with 100 pg Rspo2 or preprolactin (ppl) mRNA in each blastomere. Note ectopic cement glands (arrowhead) and shortened body axis in Rspo2 injected embryo. (FIG. 11C-J) Whole mount in situ hybridisations of the indicated genes. Eight-cell stage embryos were injected with 100 pg of Rspo2 or ppl RNAs as indicated into one animal blastomere. LacZ mRNA was coinjected as lineage tracer in all panels except FIG. 11C, FIG. 11G and FIG. 11H. (FIG. 11C-H) Stage 15 neurulae in anterior view. (FIG. 11I-J) Stage 11 gastrulae in vegetal view, dorsal up. (FIG. 11K-N) Rspo2 promotes muscle formation. (FIG. 11K) Diagram of the experiments. Four-cell stage embryos were injected with 50 pg plasmid DNA constructs in all blastomeres, the indicated fragments were explanted at stage 10.5, cultured, and processed for whole mount in situ hybridisation (FIG. 11M) of RT-PCR (FIG. 11N). (FIG. 11L) Stage 40 equivalent VMZ of LMZ explants. Note tail-like structures in VMZs from Rspo2 injected embryos. (FIG. 11M) In situ hybridization of stage 25 VMZs for muscle actin. (FIG. 11N) RT-PCR analysis for the indicated genes in stage 25 equivalent VMZ and stage 11 equivalent DMZ explants. Xdd I, dominant negative. *Xenopus* dishevelled; Co, preprolactin.

(FIG. 12A-D) Four-cell stage embryos were injected animally with indicated RNAs. At stage 8, animal caps were dissected, cultured until stage 10 equivalent and analyzed for expression of Vent2 (FIG. 12A) or Xbra (FIG. 12B-D). −RT, minus reverse transcription control. Embryos injected with 100 pg preprolactin (ppl) were used as control. Amounts of mRNAs used: 100 pg Rspo2, 50 pg or 250 pg of BMP-4, 50 pg of activin, 25 or 100 pg of Wnt8, 200 pg of β-catenin, 50 or 100 pg of Xnrl, 2 or 20 pg of FGF8.

FIG. 13A-D: *Xenopus* Rspo2 is required for muscle formation. (FIG. 13A) Rspo2Mo specifically inhibits translation of its cognate DNA. Top, Diagram of the experiment. Two-cell stage *Xenopus* embryos were injected with 100 pg Myc-tagged Rspo2 mRNA in the animal region, at 8-cell stage, the same embryos were then injected with 5 ng of Rspo2Mo of CoMo in all animal blastomeres, harvested at stage 11 and processed for Western blot analysis of Myc-tagged Rspo2 and α-tubulin. (FIG. 13Ba-l) Depletion of Rspo2 protein causes muscle defects and down-regulation of myogeneic markers. Four-cell stage embryos were injected equatorially into one blastomere with 5 ng control morpholino oligonucleotides (CoMo) or Rspo2Mo as indicated together with 50 pg ppl mRNA or 50 pg LacZ RNA as lineage tracer and analysed at tailbud of gastrula stage by in situ hybridization for the indicated genes. In (FIG. 13Ba-f) double in situ hybridization for gene of interest (dark blue) and for ppl (red) was used, (FIG. 13Ba-d) Stage 25 embryos. (FIG. 13Ba-b): myotomes, visualised by muscle actin expression show malformations an Rspo2Mo injected side (FIG. 13Bb). (FIG. 13Bc-d) Transversal section at the trunk level showing reduced muscle volume in (FIG. 13Bd). (FIG. 13Be-h): myf5 and myoD expression (dark blue) is down-regulated in the Rspo2Mo injected region (red in FIG. 13Be, FIG. 13Bf of light blue in FIG. 13Bg, FIG. 13Bh). (FIG. 13Bi-l): Xbra and Xnot2 expression (dark blue) is not affected in the region of Rspo2Mo injections (light blue). (FIG. 13C) Rspo2Mo acts specifically. Rescue of myf5 reduction by co-injected Rspo2 mRNA. Four cell stage embryos were injected in one blastomere with 5 ng of control morpholino (CoMo), Rspo2Mo, 50 pg ppl mRNA of 50 pg Rspo2 mRNA containing mismatches to Rspo2Mo. Expression of myf5 was analysed by in situ hybridization at gastrula stage. The percentage of embryos with, strongly affected (A), moderately reduced (B) and normal myf5 expression (C) as displayed in the representative embryos is indicated. Standard deviation was calculated from three independent experiments. (FIG. 13Da-d) Rspo2Mo Blocks Wnt signalling upstream of dishevel led during muscle formation. Four-cell stage embryos were radially injected with 5 ng of Rspo2Mo or CoMo, 50 pg pCS-XWnt8, pCS-dishevel led (Xdsh), pCS-dominant negative GSK-3β (dnGSK) or pCS-β-catenin. At stage 10.5 DMZs (FIG. 13Da) or VMZs (FIG. 13Db) or LMZs (FIG. 13Dc-d) were explanted and cultured until stage 11 (FIG. 13Da, FIG. 13Dc) or 25 (FIG. 13Db, FIG. 13Dd) for RT-PCR analysis of the genes indicated. –RT: minus reverse transcription control.

(FIG. 14A) RT-PCR analysis showing differential expression of human Rspo1-4 in HeLa and 293T cell lines. Actin was used for normalisation. (FIG. 14B) Specificity of siRNAs. 293T cells were cotransfected with pSUPER-Rspo2 or -3 (siRNA), FLAG-tagged Rspo3 and GFP (transfection control). Expression of Rspo3 and GFP were analyzed by Western blot. (FIG. 14C-D) R-spondins are required for Wnt/β-catenin signalling in HeLa cells. Wnt luciferase reporter assay in HeLa cells cotransfected with the indicated constructs. Wnt3a was added as conditioned medium. RLU, relative light units.

(FIG. 15A-E) The expression of Futrin 1, 2, 3 and -4 or ubiquitin (to show equal loading) was analysed by radioactive hybridisation on arrayed mRNAs (Clontech, Cancer Profiling Array II) from normal and cancerous tissue samples from different patients. Abbreviations N, normal tissues; T, tumor tissues.

(FIG. 17A-C) Wnt luciferase reporter assay in 293T cells co-transfected with the indicated constructs. Results are indicated as fold-stimulation over reporter alone. DNA doses were 5 ng Wnt1, 1 ng Fz8, 3 ng LRP6, 10 ng axin, 10 ng dntcf3, 5 ng dkk1, 10 ng Xdsh, 1 ng Wnt3a.

DETAILED DESCRIPTION

Figures 3, 3A, 3C:
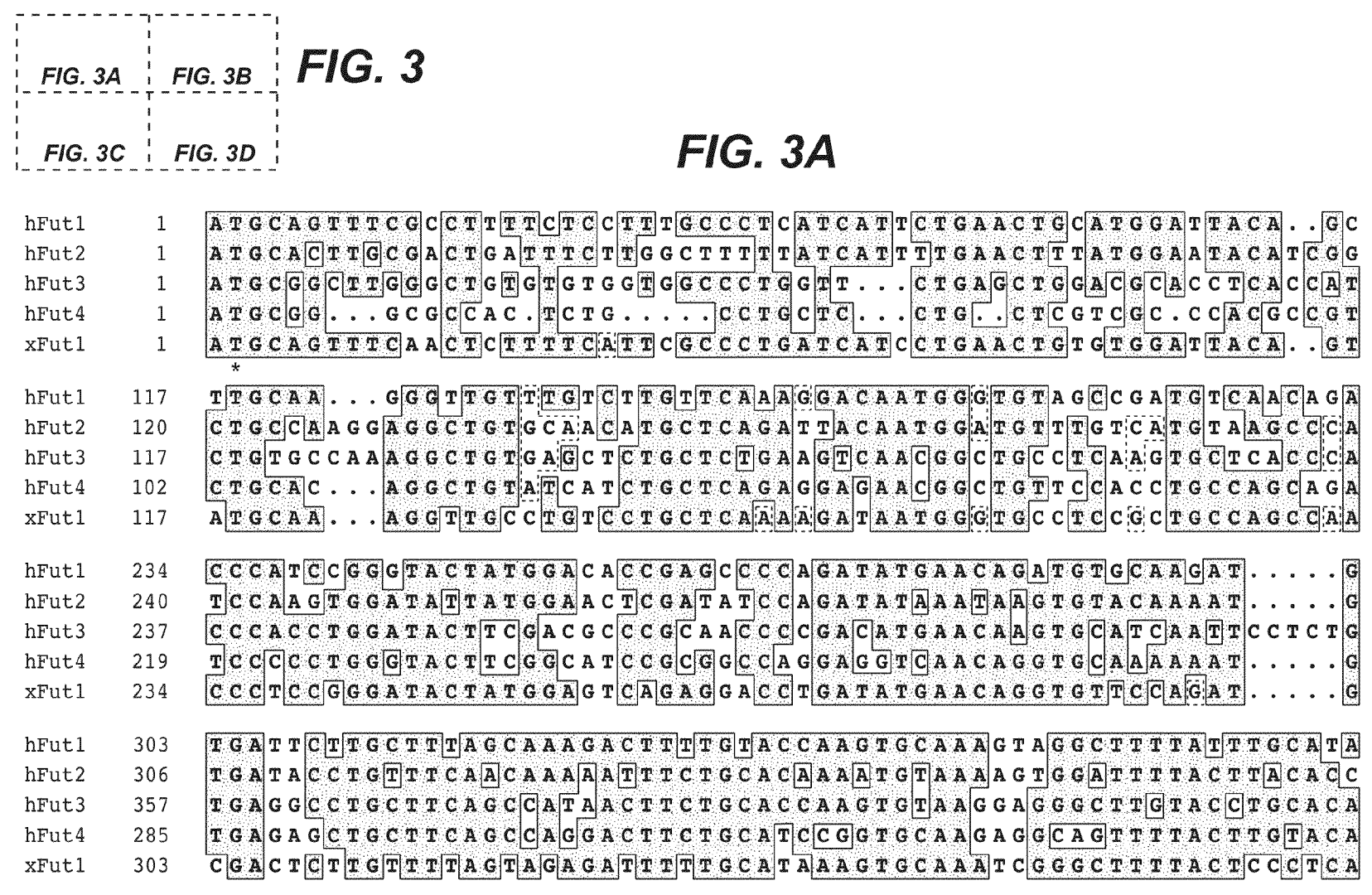
Figure 3B:
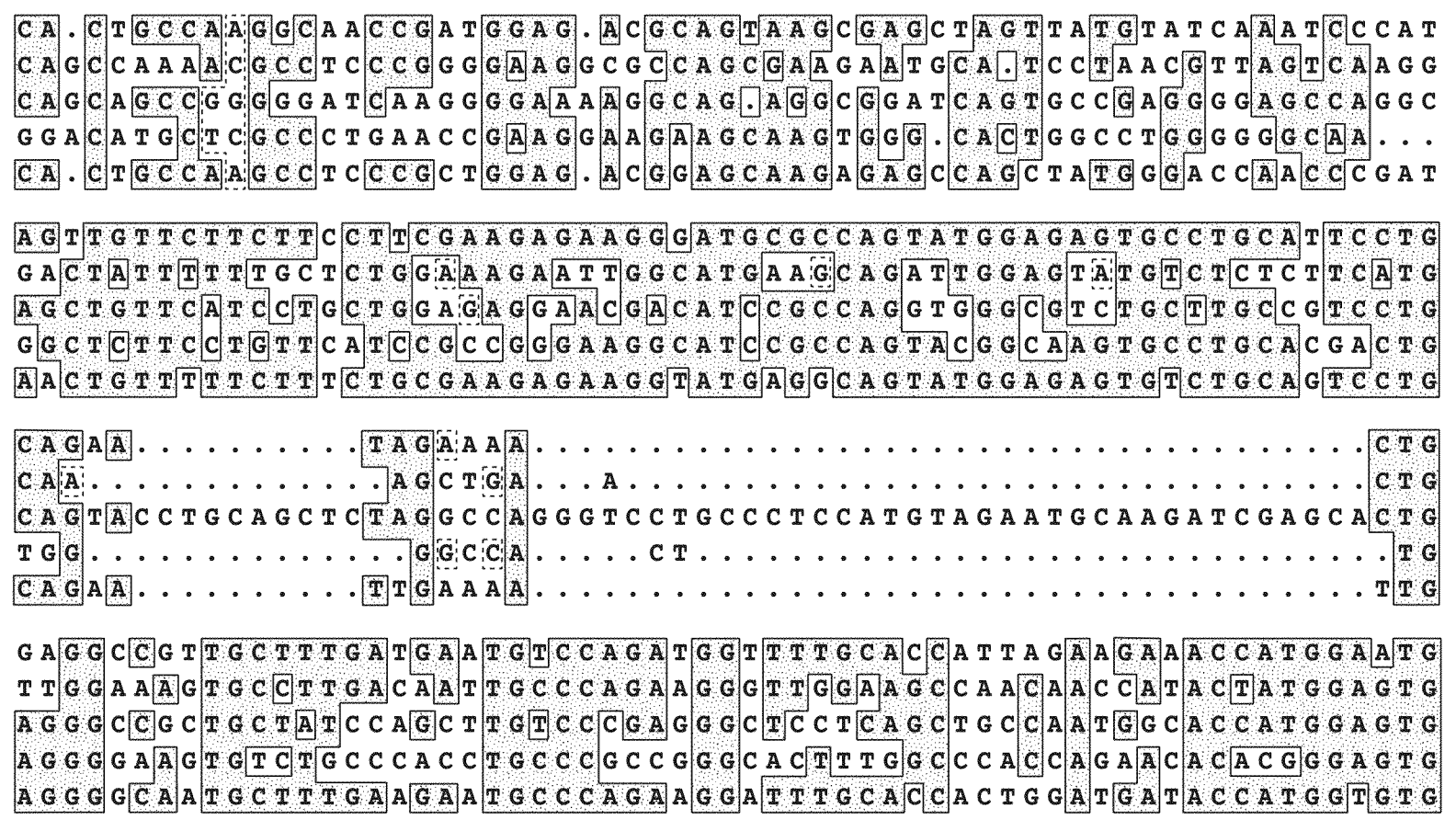
Figure 3C:
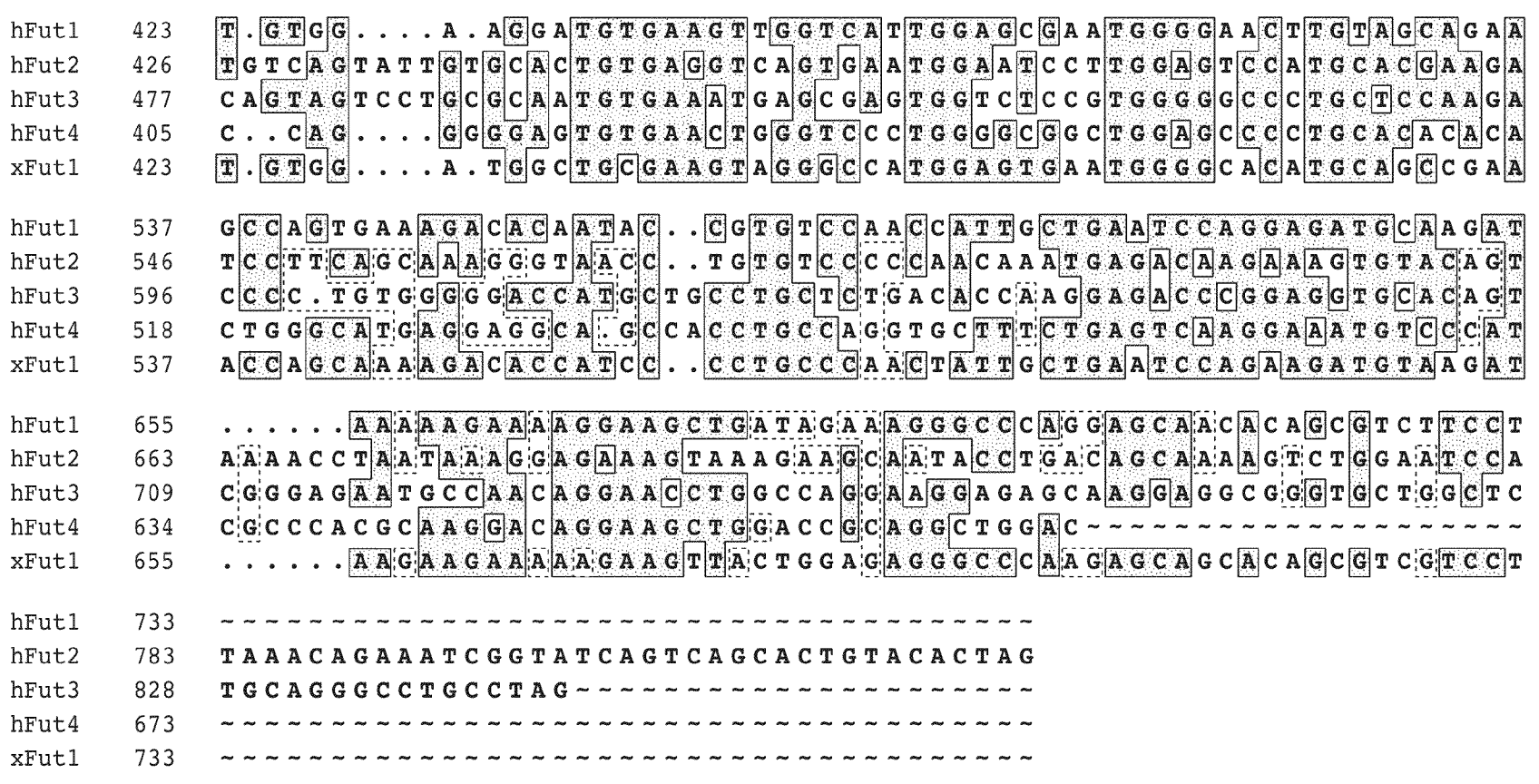
Figure 6A:
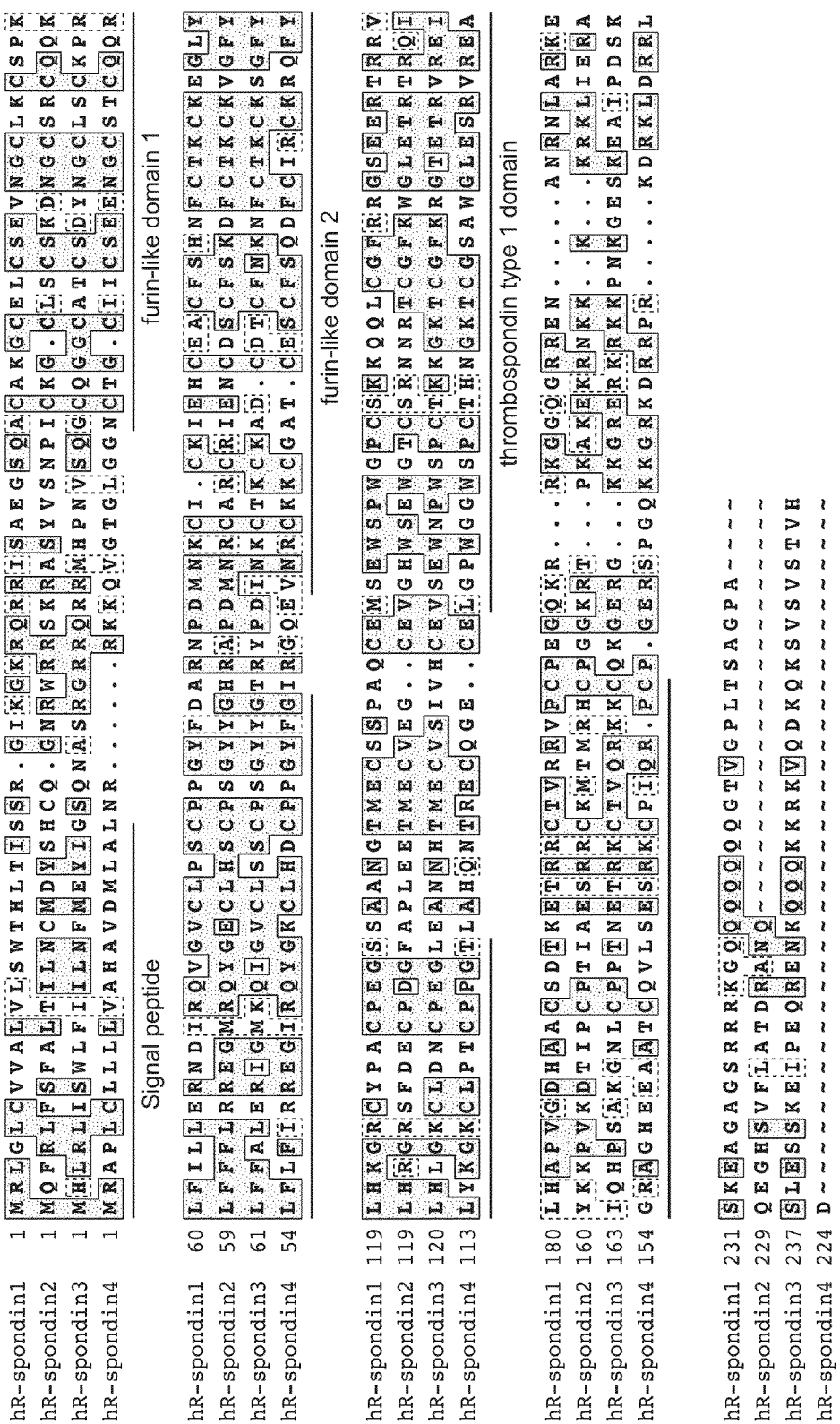

The present invention relates to a diagnostic composition comprising:
(a) at least one nucleic acid molecule comprising the nucleotide sequence encoding Futrin 1, 2, 3 or 4 as depicted in FIG. 3; and/or
(b) at least one polypeptide molecule comprising the amino acid sequence encoding Futrin 1, 2, 3 or 4 as depicted in FIG. 4 or 6a; and/or
(c) at least one nucleic acid molecule the complementary strand of which hybridizes to a nucleic acid molecule of (a) and which encodes a polypeptide with the biological activity of Futrin 1, 2, 3 or 4; and/or
(d) at least one fragment of (a), (b) or (c) having the biological activity of Futrin 1, 2, 3 or 4;
(e) at least one nucleic acid molecule the sequence of which differs from the sequence of the nucleic acid molecule of (a), (c) or (d) due to the degeneracy of the genetic code, and/or
(f) at least one ligand capable of specifically binding to the molecule of (a), (b), (c), (d) or (e).

As used herein the term "polypeptide" not only refers to polypeptides encoded by the nucleotide/amino acid sequences as depicted in FIGS. 3 and/or 4 but also to polypeptides differing in amino acid sequence due to insertion, deletion and/or substitution of one ore more amino acids and showing at least one biological activity of a Futrin, e.g. the ability to promote Wnt signalling. Preferably, the related nucleic acids and/or polypeptides are nucleic acids and/or polypeptides the sequence of which shows an identity of at least 40%, in particular an identity of at least 65%, preferably of at least 80% and, particularly preferred, of at least 90% to the amino acid sequences of the polypeptides encoded by the nucleotide sequences shown in FIG. 3.

The nucleic acid molecules useful as probes can be both DNA and RNA molecules, preferably they are single-stranded DNA molecules. They can be isolated from natural sources or can be synthesized according to know methods.

As a hybridization probe nucleic acid molecules can be used, for example, that have a nucleotide sequence which is exactly or basically complementary to a nucleotide sequence as depicted in FIGS. 3 and 4 or 6a, respectively, or parts of these sequences. The fragments used as hybridization probe can be synthetic fragments that were produced by means of conventional synthetic methods.

As used herein, the term "hybridizing" relates to hybridization under conventional hybridization conditions, preferably under stringent conditions as described, for example, in Sambrook et al., Molecular Cloning, A Laboratory Manual 2nd edition (1989) Cold Spring Harbor Laboratory Press, Cold Spring Harbor, N.Y. However, in certain cases, a hybridizing nucleic acid molecule can also be detected at lower stringency hybridization conditions. Changes in the stringency of hybridization and signal detection are primarily accomplished through the manipulation of formamide concentration (lower percentages of formamide result in lowered stringency, salt conditions, or temperature. For example, lower stringency conditions include an overnight incubation at 37° C. in a solution comprising 6×SSPE (20×SSPE=3M NaCl; 9.2M NaH$_2$PO$_4$; 0.02M EDTA, pH7.4), 0.5% SDS, 30% formamide, 100 μg/ml salmon sperm blocking DNA, following by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. The inclusion of specific blocking reagents may require modification of the hybridization conditions described above, due to problems with compatibility.

The term "ligand" as used herein refers to any molecule which is capable of specifically binding to Futrin 1, 2, 3, or 4, thus allowing to determine the level of receptor molecules. Examples of such molecules include antibodies, oligonucleotides, proteins or small molecules. The molecule can be the natural ligand of Futrins, or can be closely related to said ligand, e.g., a fragment of the ligand, or a natural substrate, a structural or functional mimetic; see, e.g., Coligan, Current Protocols in Immunology 1(2) (1991); Chapter 5. In either case, the molecule can be isolated or rationally designed using known techniques; see also infra.

Preferably, the ligand is an antibody. The term "antibody", preferably, relates to antibodies which consist essentially of pooled monoclonal antibodies with different epitopic specificities, as well as distinct monoclonal antibody preparations. Monoclonal antibodies are made from an antigen containing Futrin 1, 2, 3, or 4 or fragments thereof by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab') 2 fragments) which are capable of specifically binding to Futrin 1, 2, 3 and/or 4. Fab and f(ab')2 fragments lack the Fc fragment of intact antibody, clear more rapidly from the circulation, and may have less non-specific tissue binding than an intact antibody. (Wahl et al., J. Nucl. Med. 24: 316-325 (1983)). Thus, these fragments are preferred, as well as the products of a FAB or other immunoglobulin expression library. Moreover, antibodies of the present invention include chimerical, single chain, and humanized antibodies.

For certain purposes, e.g. diagnostic methods, the nucleic acid molecule used as probe or the ligand, e.g., antibody, can be detectably labeled, for example, with a radioisotope, a bioluminescent compound, a chemiluminescent compound, a fluorescent compound, a metal chelate, or an enzyme.

The nucleic acid molecules can be used, for example, as probes or primers in the diagnostic assays described below and allow, e.g., the analysis of the expression of Futrin 1, 2, 3, or -4 by determining the mRNA level or the determination of mutations within the coding region or regulatory regions leading to polypeptide molecules with altered, e.g. destroyed, activity, or leading to altered expression. Preferably, the nucleic acid molecules are oligonucleotides having a length of at least 10, in particular of at least 15 and particularly preferred of at least 50 nucleotides. These nucleic acid molecules of the invention can also be used, for example, as primers for a PCR reaction.

The present invention also relates to the use of a nucleic acid molecule or ligand as defined above for the preparation of a diagnostic composition for the diagnosis of a disease associated with (a) aberrant expression of Futrin 1, 2, 3, or -4 and/or (b) aberrant activity of a Futrin 1, 2, 3, or -4 polypeptide.

In a preferred embodiment, the target to which the nucleic acid molecule hybridizes is an mRNA.

The present invention also provides a method of diagnosing a disease associated with (a) aberrant expression of Futrin 1, 2, 3, or -4 and/or (b) aberrant activities or amounts of a Futrin 1, 2, 3, or -4 polypeptide in a subject comprising:
(a) determining (a) the amount of expression of Futrin 1, 2, 3, or -4 and/or (b) the amount of biologically active Futrin 1, 2, 3 and/or 4 polypeptide in a biological sample; and
(b) diagnosing a disease associated with (a) aberrant expression of Futrin 1, 2, 3 and/or 4 and/or (b) aberrant activities or amounts of a Futrin 1, 2, 3 and/or 4 polypeptide or a risk for the development of such disease based on an altered amount of expression of Futrin 1, 2, 3 and/or 4 and/or (b) altered activities or amounts of biologically active Futrin 1, 2, 3 and/or 4 polypeptide compared to a control.

Suitable assay formats are well known to the person skilled in the art and, in addition, described below. Suitable positive control samples expressing human Futrin proteins are, e.g., HEK 293 cells.

The Futrin 1, 2, 3, or 4 polypeptide or the corresponding mRNA, e.g. in biological fluids or tissues, may be detected directly in situ, e.g. by in situ hybridization or it may be isolated from other cell components by common methods known to those skilled in the art before contacting with a probe. Detection methods include Northern Blot analysis, RNase protection, in situ methods, e.g. in situ hybridization, in vitro amplification methods (PCR, LCR, QRNA replicase or RNA-transcription/amplification (TAS, 3SR), reverse dot blot disclosed in EP-B1 O 237 362), immunoassays, Western Blot and other detection assays that are known to those skilled in the art.

The probe (e.g. a specific antibody or specific oligonucleotide) of the diagnostic composition can be detectably labeled. In a preferred embodiment, said diagnostic composition contains an anti-Futrin 1, 2, 3 and/or 4 antibody and allows said diagnosis, e.g., by ELISA and contains the antibody bound to a solid support, for example, a polystyrene microtiter dish or nitrocellulose paper, using techniques known in the art. Alternatively, said diagnostic compositions are based on a RIA and contain said antibody marked with a radioactive isotope. Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium rhodamine, and biotin. In addition to assaying Futrin levels in a biological sample, the polypeptide can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. A protein-specific antibody or antibody fragment which has been labeled with an appropriate detectable imaging moiety, such as a radioisotope (for example, $^{131}$I, $^{112}$In, $^{99}$mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells which contain the specific Futrin polypeptide. In vivo tumor imaging is, e.g., described in S. W. Burchiel et al., "Immunopharmacokinetics of Radiolabeled Antibodies and Their Fragments". (Chapter 13 in Tumor Imaging: The Radiochemical Detection of Cancer, S. W. Burchiel and B. A. Rhodes, eds., Masson Publishing Inc. (1982)).

In a further aspect, the present invention, relates to a method for identifying a binding partner to a Futrin 1, 2, 3 and/or -4 polypeptide comprising:
(a) contacting-said polypeptide with a compound to be screened; and (b) determining whether the compound effects an activity of the polypeptide.

The invention also includes a method of identifying compounds which bind to a Futrin 1, 2, 3 and/or 4 polypeptide comprising the steps of:
 (a) incubating a candidate binding compound with said polypeptide; and
 (b) determining if binding has occurred.

Futrin 1, 2, 3 or -4 polypeptides may be used to screen for proteins or other compounds that bind to Futrin 1, 2, 3 or -4 or for proteins or other compounds to which Futrin1, 2, 3 and/or 4 bind. The binding of Futrin1, 2, 3 or -4 and the molecule may activate (agonist), increase, inhibit (antagonist), or decrease activity of Futrin 1, 2, 3 or 4 or the molecule bound. Examples of such molecules include antibodies, oligonucleotides, proteins (e.g., ligands), or small molecules.

Preferably, the molecule is closely related to the natural ligand of Futrin 1, 2, 3 or -4, e.g., a fragment of the ligand, or a natural substrate, a ligand, a structural or functional mimetic; see, e.g., Coligan, Current Protocols in Immunology 1(2) (1991); Chapter 5.

Preferably, the screening for these molecules involves producing appropriate cells which express Futrin 1, 2, 3 and/or 4 either as a secreted protein or on the cell membrane. Preferred cells include cells from mammals, yeast, *Drosophila*, or *E. coli*. Cells expressing Futrin 1, 2, 3 and/or -4 (or cell membrane containing the expressed polypeptide) are then preferably contacted with a test compound potentially containing the molecule to observe binding, stimulation, or inhibition of activity of Futrin 1, 2, 3 and/or -4.

The assay may simply test binding of a candidate compound to Futrin 1, 2, 3 and/or 4, wherein binding is detected by a label, or in an assay involving competition with a labeled competitor. Further, the assay may test whether the candidate compound results in a signal generated by binding to Futrin 1, 2, 3 and/or 4. Suitable assays to analyze the activity of Futrin 1, 2, 3 and/or 4 include Wnt-inducible luciferase reporter assays in transfected HEK 293 cells, where Futrin 1, 2, 3 and/or 4 synergizes with Wnt to enhance a Wnt-induced signal, such as is shown in FIG. 4.

Alternatively, the assay can be carried out using cell-free preparations, polypeptide/molecule affixed to a solid support, chemical libraries, or natural product mixtures. The assay may also simply comprise the steps of mixing a candidate compound with a solution containing Futrin 1, 2, 3 and/or 4, measuring Futrin/molecule activity or binding, and comparing the Futrin/molecule activity or binding to a standard.

Preferably, an ELISA assay can measure Futrin 1, 2, 3 and/or 4 level or activity in a sample (e.g., biological sample) using a monoclonal or polyclonal antibody. The antibody can measure Futrin 1, 2, 3 and/or 4 level or activity by either binding, directly or indirectly, to Futrin 1, 2, 3 and/or 4 or by competing with Futrin 1, 2, 3 and/or 4 for a substrate. All of these above assays can be used as diagnostic or prognostic markers. The molecules discovered using these assays can be used to treat disease or to bring about a particular result in a patient (e.g., elimination of a tumor, support of regenerative processes etc.) by modulating, preferably activating the Futrin 1, 2, 3 and/or 4 molecule. Moreover, the assays can discover agents which may inhibit or enhance the production of Futrin 1, 2, 3 and/or 4 from suitably manipulated cells or tissues.

Moreover, the invention includes a method of identifying activators/agonists or inhibitors/antagonists of a Futrin 1, 2, 3 and/or 4 polypeptide comprising the steps of:
 (a) incubating a candidate compound with said polypeptide;
 (b) assaying a biological activity, and
 (c) determining if a biological activity of said polypeptide has been altered.

Suitable assays to analyze the activity of Futrin 1, 2, 3 and/or 4 include Wnt-inducible luciferase reporter assays in transfected HEK 293 cells, where Futrin 1, 2, 3 and/or 4 synergizes with Wnt to enhance a Wnt-induced signal, such as is shown in FIG. 4.

In a further embodiment, the present invention relates to method of identifying and obtaining a drug candidate for therapy of diseases associated with (a) aberrant expression of Futrin 1, 2, 3 and/or 4 and/or (b) aberrant activities or amounts of a Futrin 1, 2, 3 and/or 4 polypeptide comprising the steps of
 (a) contacting a Futrin 1, 2, 3 and/or 4 polypeptide or a cell expressing said polypeptide, and optionally the corresponding ligand (s), in the presence of components capable of providing a detectable signal in response to binding to said drug candidate to be screened; and
 (b) detecting presence or absence of a signal or increase of the signal generated, wherein the presence or increase of the signal is indicative for a putative drug.

Suitable assays to analyze the activity of Futrin 1, 2, 3 and/or 4 include Wnt-inducible luciferase reporter assays in transfected HEK 293 cells, where Futrin 1, 2, 3 and/or 4 synergizes with Wnt to enhance a Wnt-induced signal, such as is shown in FIG. 4.

The drug candidate may be a single compound or a plurality of compounds. The term "plurality of compounds" in a method of the invention is to be understood as a plurality of substances which may or may not be identical.

Said compound or plurality of compounds may be chemically synthesized or microbiologically produced and/or comprised in, for example, samples, e.g., cell extracts from, e.g., plants, animals or microorganisms. Furthermore, said compound(s) may be known in the art but hitherto not known to be capable of suppressing or activating Futrin1, 2, 3 and/or 4 polypeptides. The reaction mixture may be a cell free extract or may comprise a cell or tissue culture. Suitable set ups for the method of the invention are known to the person skilled in the art and are, for example, generally described in Alberts et al., Molecular Biology of the Cell, third edition (1994) and in the appended examples. The plurality of compounds may be, e.g., added to the reaction mixture, culture medium, injected into a cell or otherwise applied to a transgenic animal. The cell or tissue that may be employed in the method of the invention preferably is a host cell, mammalian cell or non-human transgenic animal.

If a sample containing a compound or a plurality of compounds is identified in the method of the invention, then it is either possible to isolate the compound from the original sample identified as containing the compound capable of suppressing or activating a Futrin 1, 2, 3 and/or 4 polypeptide, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical.

Several methods are known to the person skilled in the art for producing and screening large libraries to identify compounds having specific affinity for a target. These methods include the phage-display method in which randomized peptides are displayed from phage and screened by affinity chromatography to an immobilized receptor; see, e.g., WO 91/17271, WO 92/01047, U.S. Pat. No. 5,223,409. In another approach, combinatorial libraries of polymers immobilized on a chip are synthesized using photolithography; see, e.g., U.S. Pat. No. 5,143,854, WO 90/15070 and WO 92/10092. The immobilized polymers are contacted with a labeled receptor and scanned for label to identify polymers binding to the receptor. The synthesis and screening of peptide libraries on continuous cellulose membrane supports that can be used for identifying binding ligands of the Futrin1, 2, 3 and/or -4 polypeptides and, thus, possible inhibitors and activators is described, for example, in Kramer, Methods Mol. Biol. 87 (1998), 25-39. This method can also be used, for example, for determining the binding sites and the recognition motifs in the Futrin 1, 2, 3 and/or -4 polypeptide. In like manner, the substrate specificity of the DnaK chaperon was determined and the contact sites between human interleukin-6 and its receptor; see Rudiger, EMBO J. 16 (1997), 1501-1507 and Weiergraber, FEBS Lett. 379 (1996), 122-126, respectively. Furthermore, the above-mentioned methods can be used for the construction of binding supertopes derived from the Futrin 1, 2, 3 or 4 polypeptide. A similar approach was successfully described for peptide antigens of the anti-p24 (HIV-1) monoclonal antibody; see Kramer, Cell 91 (1997), 799-809. A general route to fingerprint analyses of peptide-antibody interactions using the clustered amino acid peptide library was described in Kramer, Mol. Immunol. 32 (1995), 459-465. In addition, antagonists of a Futrin 1, 2, 3 and/or 4 polypeptide can be derived and identified from monoclonal antibodies that specifically react with a Futrin 1, 2, 3 and/or 4 polypeptide in accordance with the methods as described in Doring, Mol. Immunol. 31 (1994), 1059-1067.

All these methods can be used in accordance with the present invention to identify activators/agonists and inhibitors/antagonists of a Futrin 1, 2, 3 and/or 4 polypeptide.

Various sources for the basic structure of such an activator or inhibitor can be employed and comprise, for example, mimetic analogs of a Futrin 1, 2, 3 and/or 4 polypeptide. Mimetic analogs of a Futrin 1, 2, 3 and/or 4 polypeptide or biologically active fragments thereof can be generated by, for example, substituting the amino acids that are expected to be essential for the biological activity with, e.g., stereoisomers, i.e. D-amino acids; see e.g., Tsukida, J. Med. Chem. 40 (1997), 3534-3541. Furthermore, in case fragments are used for the design of biologically active analogs pro-mimetic components can be incorporated into a peptide to reestablish at least some of the conformational properties that may have been lost upon removal of part of the original polypeptide; see, e.g., Nachman, Regul. Pept. 57 (1995), 359-370. Furthermore, a Futrin 1, 2, 3 and/or 4 polypeptide can be used to identify synthetic chemical peptide mimetics that bind to or can function as a ligand, substrate or binding partner of said polypeptide(s) as effectively as does the natural polypeptide; see, e.g., Engleman, J. Clin. Invest. 99 (1997), 2284-2292. For example, folding simulations and computer redesign of structural motifs of a Futrin 1, 2, 3 and/or 4 polypeptide can be performed using appropriate computer programs (Olszewski, Proteins 25 (1996), 286-299; Hoffman, Comput. Appl. Biosci. 11 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of a Futrin 1, 2, 3 and/or 4 polypeptide and its ligand or other interacting proteins by computer assistant searches for complementary peptide sequences (Fassina, Immunomethods 5 (1994), 114-120. Further appropriate computer systems for the design of protein and peptides are described in the prior art, for example in Berry, Biochem. Soc. Trans. 22 (1994), 1033-1036; Wodak, Ann. N. Y. Acad. Sci. 501 (1987), 1-13; Pabo, Biochemistry 25 (1986), 5987-5991. The results obtained from the above-described computer analysis can be used for, e.g., the preparation of peptide mimetics of a Futrin 1, 2, 3 and/or 4 polypeptide or fragments thereof. Such pseudopeptide analogues of the natural amino acid sequence of the protein may very efficiently mimic the parent protein (Benkirane, J. Biol. Chem. 271 (1996), 33218-33224). For example, incorporation of easily available achiral ω-amino acid residues into a Futrin 1, 2, 3 or -4 polypeptide or a fragment thereof results in the substitution of amide bonds by polymethylene units of an aliphatic chain, thereby providing a convenient strategy for constructing a peptide mimetic (Banerjee, Biopolymers 39 (1996), 769-777). Superactive peptidomimetic analogues of small peptide hormones in other systems are described in the prior art (Zhang, Biochem. Biophys. Res. Commun. 224 (1996), 327-331). Appropriate peptide mimetics of a Futrin 1, 2, 3 and/or 4 polypeptide can also be identified by the synthesis of peptide mimetic combinatorial libraries through successive amide alkylation and testing the resulting compounds, e.g., for their binding and immunological properties. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, a three-dimensional and/or crystallographic structure of a Futrin 1, 2, 3 and/or 4 polypeptide can be used for the design of peptide mimetic inhibitors of the biological activity of the polypeptide (Rose, Biochemistry 35 (1996), 12933-12944; Rutenber, Bioorg. Med. Chem. 4 (1996), 1545-1558).

It is also well known to the person skilled in the art, that it is possible to design, synthesize and evaluate mimetics of small organic compounds that, for example, can act as a substrate or ligand to a Futrin 1, 2, 3 and/or 4 polypeptide. For example, it has been described that D-glucose mimetics of hapalosin exhibited similar efficiency as hapalosin in antagonizing multidrug resistance assistance-associated protein in cytotoxicity; see Dinh, J. Med. Chem. 41 (1998), 981-987.

The nucleic acid molecule encoding a Futrin 1, 2, 3 and/or 4 polypeptide can also serve as a target for activators and inhibitors. Activators may comprise, for example, proteins that bind to the mRNA of a gene encoding a Futrin 1, 2, 3 and/or 4 polypeptide, thereby stabilizing the native conformation of the mRNA and facilitating transcription and/or translation, e.g., in like manner as Tat protein acts on HIV-RNA. Furthermore, methods are described in the literature for identifying nucleic acid molecules such as an RNA fragment that mimics the structure of a defined or undefined target RNA molecule to which a compound binds inside of a cell resulting in retardation of cell growth or cell death; see, e.g., WO 98/18947 and references cited therein. These nucleic acid molecules can be used for identifying unknown compounds of pharmaceutical interest, and for identifying unknown RNA targets for use in treating a disease. These methods and compositions can be used in screening for novel or for identifying compounds useful to alter expression levels of polypeptides encoded by a nucleic acid molecule. Alternatively, for example, the conformational structure of the RNA fragment which mimics the binding site can be employed in rational drug design to modify known drugs to make them bind more avidly to the target. One such methodology is nuclear magnetic resonance (NMR), which is useful to identify drug and RNA conformational structures. Still other methods are, for example, the drug design methods as described in WO 95/35367, U.S. Pat. No. 5,322,933, where the crystal structure of the RNA fragment can be deduced and computer programs are utilized to design novel binding compounds.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Furthermore, genes encoding a putative regulator of a Futrin 1, 2, 3 and/or 4 polypeptide and/or which exert their effects up- or downstream a Futrin 1, 2, 3 and/or 4 polypeptide may be identified using, for example, insertion mutagenesis using, for example, gene targeting vectors known in the art. Said compounds can also be functional derivatives or analogues of known inhibitors or activators. Such useful compounds can be for example transacting factors which bind to a Futrin 1, 2, 3 and/or 4 polypeptide or regulatory sequences of the gene encoding it. Identification of transacting factors can be carried out using standard methods in the art (see, e.g., Sambrook, supra). To determine whether a protein binds to the protein itself or regulatory sequences, standard native gel-shift analyses can be carried out. In order to identify a transacting factor which binds to the protein or regulatory sequence, the protein or regulatory sequence can be used as an affinity reagent in standard protein purification methods, or as a probe for screening an expression library. The identification of nucleic acid molecules which encode polypeptides which interact with a Futrin 1, 2, 3 and/or 4 polypeptide described above can also be achieved, for example, as described in Scofield (Science 274 (1996), 2063-2065) by use of the so-called yeast "two-hybrid system". In this system the Futrin1, 2, 3 or 4 polypeptide or a smaller part thereof is linked to the DNA-binding domain of the GAL4 transcription factor. A yeast strain expressing this fusion polypeptide and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of a Futrin 1, 2, 3 and/or 4 polypeptide, the complex is able to direct expression of the reporter gene. In this way the nucleic acid molecules encoding Futrin1, 2, 3 and 4, respectively, and the encoded peptide can be used to identify peptides and proteins interacting with a Futrin1, 2, 3 and/or 4 polypeptide.

Once the transacting factor is identified, modulation of its binding to or regulation of expression of a Futrin 1, 2, 3 and/or 4 polypeptide can be pursued, beginning with, for example, screening for inhibitors against the binding of the transacting factor to a Futrin1, 2, 3 or 4 polypeptide. Activation or repression of a Futrin 1, 2, 3 and/or 4 polypeptide could then be achieved in animals by applying the transacting factor (or its inhibitor) or the gene encoding it, e.g. in an expression vector. In addition, if the active form of the transacting factor is a dimer, dominant-negative mutants of the transacting factor could be made in order to inhibit its activity. Furthermore, upon identification of the transacting factor, further components in the signal cascade leading to activation (e.g. signal transduction) or repression of a gene involved in the control of a Futrin 1, 2, 3 and/or 4 polypeptide then can be identified. Modulation of the activities of these components can then be pursued, in order to develop additional drugs and methods for modulating the metabolism of protein degradation in animals. Thus, the present invention also relates to the use of the two-hybrid system as defined above for the identification of activators or inhibitors of a Futrin 1, 2, 3 and/or 4 polypeptide.

The compounds isolated by the above methods also serve as lead compounds for the development of analog compounds. The analogs should have a stabilized electronic configuration and molecular conformation that allows key functional groups to be presented to a Futrin 1, 2, 3 and/or 4 polypeptide or its ligand in substantially the same way as the lead compound. In particular, the analog compounds have spatial electronic properties which are comparable to the binding region, but can be smaller molecules than the lead compound, frequently having a molecular weight below about 2 kD and preferably below about 1 kD. Identification of analog compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art; see also supra. Furthermore, peptidomimetics and/or computer aided design of appropriate derivatives and analogues can be used, for example, according to the methods described above.

Once the described compound has been identified and obtained, it is preferably provided in a therapeutically acceptable form.

Accordingly, the present invention also relates to a pharmaceutical composition comprising a nucleic acid molecule encoding a Futrin 1, 2, 3 and/or 4 polypeptide, a Futrin 1, 2, 3 and/or 4 polypeptide itself, recombinant vector (for examples, see below), antibody, activator/agonist, inhibitor/antagonist and/or binding partner of a Futrin 1, 2, 3 and/or 4 polypeptide and a pharmaceutically acceptable excipient, diluent or carrier.

Figure 1:
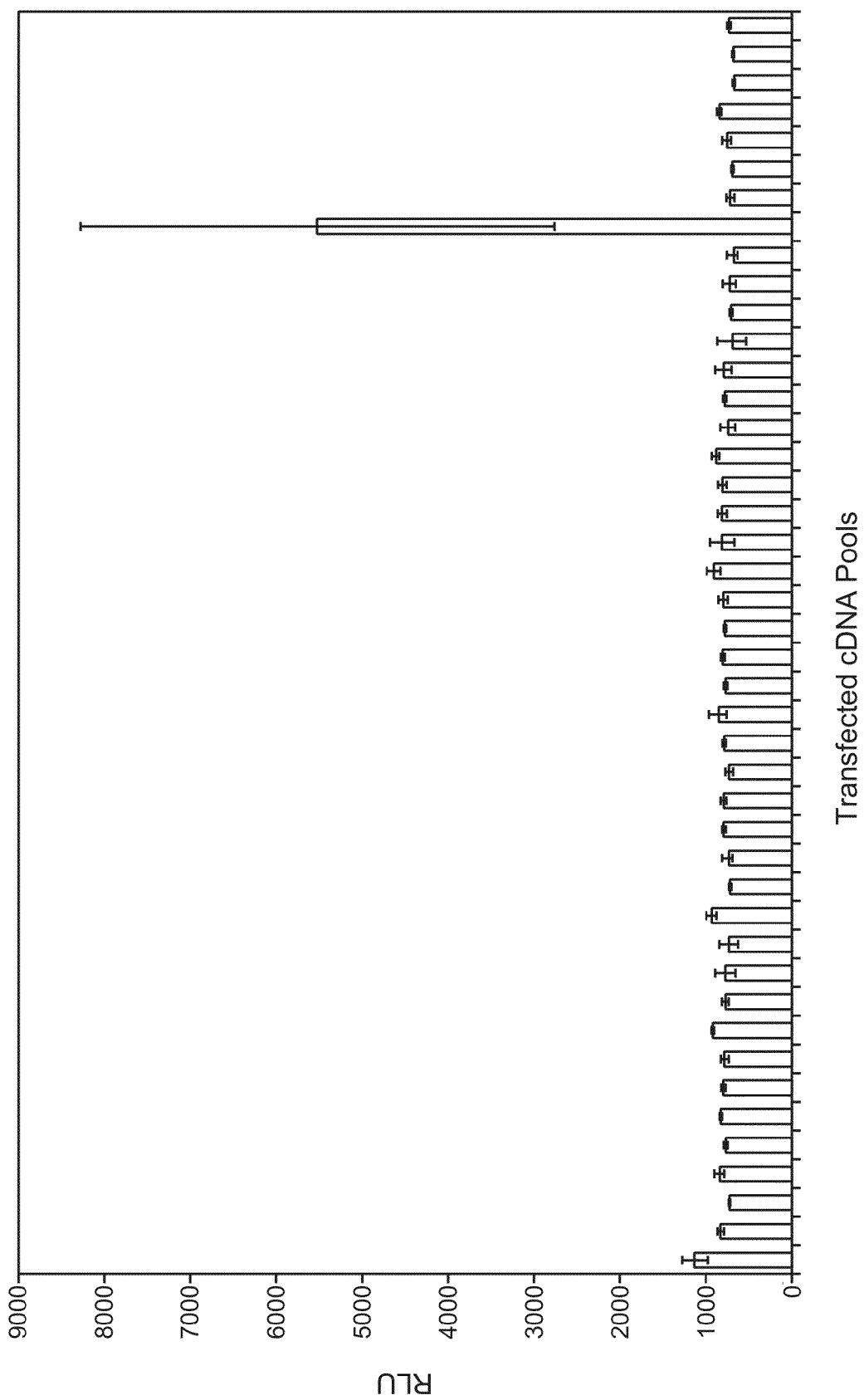
FIG. 1: Identification of *Xenopus* Futrin 1 (Rspo2). TOP-FLASH reporter, vector DNA from pools of 250 clones each and pCSfrizzled8 were co-transfected. Luciferase reporter assays in 293T cells were carried out in 96 well plates in duplicates as described (Wu et al., Curr Biol 10 (2000), 1611-1614). Luciferase activity was normalized against cotransfected Renilla-luc activity using a commercial kit (Clonetech). RLU: relative luciferase units.

Preferably, for therapeutic purposes, the Futrin 1, 2, 3 and/or 4 polypeptide is recombinantly produced by use of the nucleic acid sequences shown in FIGS. 1 and 2. Suitable vectors for recombinant expression are known to the person skilled in the art. Preferably, they are plasmids, cosmids, viruses, bacteriophages and other vectors usually used in the field of genetic engineering. Vectors suitable for use in the present invention include, but are not limited to the T7-based expression vector for expression in mammalian cells and baculovirus-derived vectors for expression in insect cells. Preferably, the nucleic acid molecule of the invention is operatively linked to the regulatory elements in the recombinant vector of the invention that guarantee the transcription and synthesis of an mRNA in prokaryotic and/or eukaryotic cells that can be translated. The nucleotide sequence to be transcribed can be operably linked to a promoter like a T7, metallothionein I or polyhedrin promoter. The host cells used for recombinant expression are prokaryotic or eukaryotic cells, for example mammalian cells, bacterial cells, insect cells or yeast cells. The polypeptide is isolated from the cultivated cells and/or the culture medium. Isolation and purification of the recombinantly produced polypeptide may be carried out by conventional means including preparative chromatography and affinity and immunological separations using, e.g., an anti-Futrin 1, 2, 3 or -4 antibody, or, e.g., can be substantially purified by the one-step method described in Smith and Johnson, Gene 67; 31-40 (1988).

Examples of suitable pharmaceutical carriers etc. are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the suitable compositions may be effected by different ways, e.g. by intravenous, intraperetoneal, subcutaneous, intramuscular, topical or intradermal administration. The route of administration, of course, depends on the nature of the disease and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and stage of the disease, e.g., tumor, general health and other drugs being administered concurrently.

The delivery of the nucleic acid molecules encoding a Futrin 1, 2, 3 and/or 4 polypeptide can be achieved by direct application or, preferably, by using a recombinant expression vector such as a chimeric virus containing these compounds or a colloidal dispersion system. Direct application to the target site can be performed, e.g., by ballistic delivery, as a colloidal dispersion system or by catheter to a site in artery. The colloidal dispersion systems which can be used for delivery of the above nucleic acid molecules include macromolecule complexes, nanocapsules, microspheres, beads and lipid-based systems including oil-in-water emulsions (mixed), micelles, liposomes and lipoplexes, The preferred colloidal system is a liposome. Organ-specific or cell-specific liposomes can be used in order to achieve delivery only to the desired tissue. The targeting of liposomes can be carried out by the person skilled in the art by applying commonly known methods. This targeting includes passive targeting (utilizing the natural tendency of the liposomes to distribute to cells of the RES in organs which contain sinusoidal capillaries) or active targeting (for example by coupling the liposome to a specific ligand, e.g., an antibody, a receptor, sugar, glycolipid, protein etc., by well known methods). In the present invention monoclonal antibodies are preferably used to target liposomes to specific tissues, e.g. tumor tissue, via specific cell-surface ligands.

Preferred recombinant vectors useful for gene therapy are viral vectors, e.g. adenovirus, herpes virus, vaccinia, or, more preferably, an RNA virus such as a retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957.

In order to achieve expression only in the tar-get organ, e.g., a tumor to be treated, the nucleic acid molecules encoding a Futrin 1, 2, 3 and/or 4 polypeptide can be linked to a tissue specific promoter and used for gene therapy. Such promoters are well known to those skilled in the art (see e.g. Zimmermann et al., (1994) Neuron 12, 11-24; Vidal et al.; (1990) EMBO J. 9, 833-840; Mayford et al., (1995), Cell 81, 891-904; Pinkert et al., (1987) Genes & Dev. 1, 268-76).

The present invention also relates to the use of the above compounds of the invention for the preparation of a pharmaceutical composition for treatment of a disease associated with (a) aberrant expression of Futrin 1, 2, 3 and/or 4 and/or genes involved into the Wnt signal cascade, and/or (b) aberrant activities or amounts of a Futrin 1, 2, 3 and/or 4 and/or a polypeptide involved into the Wnt signal cascade. In a preferred embodiment, said disease is a kidney, bone or muscle disease or tumor, preferably breast cancer, a colon carcinoma or a melanoma.

Finally, the present invention relates to the use of a nucleotide molecule encoding a polypeptide having a biological activity of Futrin 1, 2, 3 and/or 4, a Futrin 1, 2, 3 and/or 4 polypeptide, an activator/agonist of a Futrin 1, 2, 3 and/or 4 polypeptide or binding partner of said polypeptide (s) for the preparation of a pharmaceutical composition for inhibiting the Wnt signal cascade which might be useful for supporting regenerative processes in a patient, e.g. growth of tissue like muscle, bone, hair, etc.

The following examples illustrate the invention.

Example 1

Materials and Methods (A) Isolation of Futrins (=R-spondins) and Constructs

A *Xenopus* adult eye cDNA library in pCS2+ was used to prepare pools of about 250 colonies. Plasmid DNA from each pool was transiently transfected into 293T cells together with the Wnt receptor frizzled8, the Wnt reporter TOPFLASH (Korinek et al., Science 275 (1997), 1784-7) and pRL-TK (Promega) using FuGENE6 (Roche) transfection reagent. Luciferase assay was carried out 24 hours after transfection. A positive clone was isolated from the pool by sib selection. Human Rspo2 and 3 cDNAs were obtained from RZPD. Fragments of hRspo1 and 4 were RT-PCR amplified from mRNA of 293T cells and used as hybridization probes. Full length mouse Rspo1 and 2 were isolated from a mouse embryonic day 13.5 cDNA library. The sequence of *X. tropicalis* Rspo3 was obtained from Sanger Institute database and a cDNA fragment was cloned by RT-PCR from *X. tropicalis* embryos. C-terminally Myc or FLAGtagged constructs and all deletion constructs were created by PCR. *Xenopus* Rspo2ΔC was cloned by deleting the last 37 amino acids. The Rspo3 cDNAs were cloned in pCS2+ and Bluescript vectors for use in gene expression and as probes, respectively.

(B) Cell Culture, Recombinant Proteins and Luciferase Reporter Assays

HEK293T, SHEP and HeLa cell lines were maintained in DMEM, 10% FCS and 10% $CO_2$. *Xenopus* Rspo2ΔC conditioned medium was produced by transient transfection in 293T cells. Mouse Wnt3a conditioned medium was produced from mouse L cells stably transfected with Wnt3a (ATCC#CRL-2647) (Shibamoto et al., Genes Cells 3 (1998), 659-670). Luciferase reporter assays in 293T cells were carried out in 96-well plates as described (Wu et al., Curr. Biol. 10 (2000), 1611-1614). Luciferase reporter assays in HeLa cells were carried out in 24 well plates in triplicates using Lipofectamine Plus transfection reagent (Invitrogen). Per well a total of 400 ng DNA were transfected, including 80 ng 7lef-fos-Luc (Novak et al., PNAS 95 (1998), 4374-4379), 10 ng pRL-TK, 10 ng mouse frizzled8, 2 ng mouse lef1 and 300 ng pSuper plasmid DNAs. 3 days after transfection, either mouse Wnt3a conditioned medium or medium containing 30 mM LICI was added to stimulate Wnt signalling. 24 hours later, luciferase activity was determined using the Dual luciferase system (Promega).

(C) Embryos, Explants, In Situ Hybridization and RNA Synthesis

In vitro fertilisation, embryo culture, staging, microinjection and culture of *Xenopus* embryo explants were carried out as described (Gawantka et al., EMBO J. 14 (1995), 6268-79). Double- and single-labeling whole-mount in situ hybridization was carried out according to (Bradley et al., Development 122 (1996), 2739-50). A PCR fragment of tropicalis Rspo3 cDNA was used for in situ hybridization on *Xenopus laevis* embryos. For vibratome sectioning, embryos were placed in embedding medium (0.4% gelatine, 30% albumin, 20% sucrose in PBS) and mounted in the presence of 2% glutaraldehyde. Sectioning was carried out using a VT100E vibratome (Leica). Brains of 4 day *Xenopus* embryos were excised in 1× Barth solution and fixed for in situ hybridisation. Whole-mount in situ hybridisation of mouse embryos was performed according to previously described procedures (Koop et al., Mech. Dev. 59 (1996), 73-78). Preparation of mRNA for *Xenopus* injections was carried out using the MegaScript in vitro transcription kit (Ambion), according to the manufacturer's instructions.

(D) Morpholino Antisense Oligonucleotides and siRNA Constructs

The 5' nucleotide sequence of an additional (pseudo-) allele for *Xenopus* Rspo2 gene was obtained using 5' RACE (GeneRacer kit, Invitrogen). Based on these sequences, an antisense morpholino oligonucleotide targeting both pseudoalleles around the ATG start codon was designed (Rspo2Mo): GCCGTCCAAATGCAGTTTCAAC (SEQ ID NO:1). pSuper constructs producing siRNA against human Rspo 2, 3 or a non-sense control were made according to Brummelkamp et al., Science 296 (2002), 550-3. The sequences are: human Rspo2, TCCCATTTGCAAGGGT-TGT (SEQ ID NO:2); human Rspo3, AGCTGACTGT-GATACCTGT (SEQ ID NO:3); nonsense control, ACTAC-CGTTGTTATAGGTG (SEQ ID NO:4).

(E) Immunohistochemistry, Western Blot and Dot Blot Analysis

Immunohistochemistry to detect β-catenin in SHEP cells was carried out according to (Scheiffele et al., J. Cell. Biol. 140 (1998), 795-806) using anti-β-catenin antibody (Transduction laboratories, Newington). For detection of tagged Rspo proteins or loading controls on Western blot, anti-Myc (clone 9E10), anti-FLAG (M2, SIGMA) monoclonal antibodies, chick anti-GFP (Chemicon, Hampshire) and mouse anti-α-tubulin (SIGMA) antibodies were used. Chemiluminescence detection (SuperSignal® solution, Pierce) was carried out according to the manufacturer's instructions after incubation of blots with anti-mouse IgG-HRP (Pierce). For Rspo expression analysis in tumour samples the Cancer Profiling Array II (Clontech, Palo Alto) was used and hybridization was carried out according the manufacturer's instructions.

(F) RT-PCR

RT-PCR assays were carried out as described (Dosch et al., Development 124 (1997), 2325-34; Glinka et al., Nature 389 (1997), 517-519); additional primers were: *Xenopus* Rspo2 (forward, GAATGCCCAGAAGGATTTGC (SEQ ID NO:5); reverse, GGGATGGTGTCTTTTGCTGG (SEQ ID NO:6)); *Xenopus* Rspo3 (forward, GAAGCAAATTGGAGTCT-GTCG (SEQ ID NO:7); reverse, GATTGTTCTCAAAC-CCTTCAGG (SEQ ID NO:8)); human Rspo1 (forward, ACAGACACAAGACACACACGC (SEQ ID NO:9); reverse, TGTCTTCTGGTGGCCTCAG (SEQ ID NO:10)); human Rspo2 (forward, CCGAGCCCCAGATATGAAC (SEQ ID NO:11); reverse, TGACCAACTTCACATCCT-TCC (SEQ ID NO:12)); human Rspo3 (forward, AGGGACT-GAAACACGGGTC (SEQ ID NO:13); reverse, TGTCT-TCTGGTGGCCTCAG (SEQ ID NO:14)); human Rspo4 (forward, AAGCTGGGACACAGCACAG (SEQ ID NO:15); reverse, GAAGCCTTGGAGCCTTGTC (SEQ ID NO:16)).

Example 2

Isolation of a cDNA Encoding *Xenopus* Futrin 1

A *Xenopus* adult eye cDNA library in the expression vector pCS2+ was used to prepare pools of about 250 colonies, and plasmid DNA from each pool was transiently transfected into 293T cells together with the Wnt receptor frizzled8, the Wnt reporter TOP-FLASH (Korinek et al. Science 275 (1997) 1784-1787) and Renilla-luciferase for normalization, in 96-well plates using FuGENE 6 (Roche, Basel). After 24 hours relative luciferase activity was determined. One pool yielding a signal above background was identified (FIGS. 1 and 2A) and a gene harboring this activity was isolated from the pool by sib selection. Sequencing analysis showed it represents *Xenopus* futrin 1. Database searches revealed four closely related genes in human, called hfutrin 1, 2, 3 and 4 (FIGS. 3A-D and 4 or 6A).

*Xenopus* futrin 1 (Rspo2) is predicted to encode a secreted protein with 243 amino acids (mature protein) and an isoelectric point of 9.8. All R-spondins contain an N-terminal signal peptide (SP), two furin-like domains (FU), one thrombospondin type1 domain (TSP1) and a C-terminal low complexity region enriched with positively charged amino acids (C) (FIG. 2F). The furin-like cysteine rich domain is found in e.g. furin-like endoproteases, EGF receptor and insulin receptor. In signal transduction by certain receptor tyrosine kinases furin repeats are required for receptor aggregation. TSP1 repeats are found in Thrombospondin and other extracellular matrix proteins like Mindin, F-spondin, SCO-spondin as well as in a number of proteins involved in the complement cascade. Proteins containing TSP1 repeats are involved in cell-cell interaction, inhibition of angiogenesis and apoptosis (Adams and Tucker, Dev. Dyn. 218 (2000), 280-99).

While *Xenopus* Rspo2 contains a predicted N-terminal signal peptide, secreted protein is almost undetectable in the medium of transiently transfected 293T cells. Since the C-terminus is enriched with basic amino acids, which promotes cell surface retention a C-terminally truncated protein was tested. Rspo2ΔC is effectively secreted into the medium from 293T cells (FIG. 2B) and is functionally active (FIG. 2F). Since all R-spondins share the basic C-terminus and since there are no obvious ER- or Golgi retention signals, this suggests that the proteins are normally associated with the cell surface.

Example 3

Futrins Promote Wnt Signalling

Figure 2A:
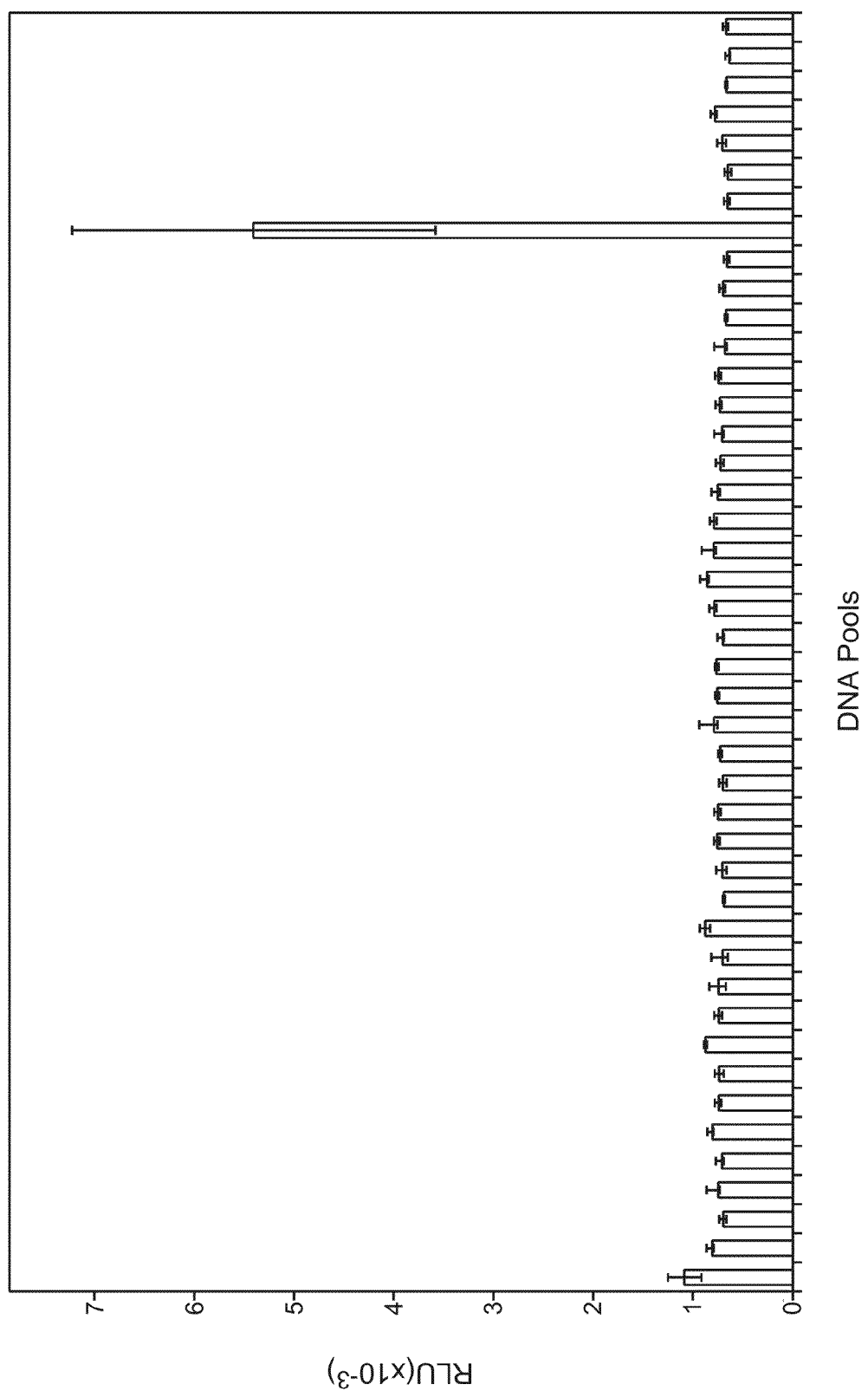
FIG. 2A-F: Futrin 1 (Rspo2) promotes Wnt/β-catenin signaling.
Figure 2B:
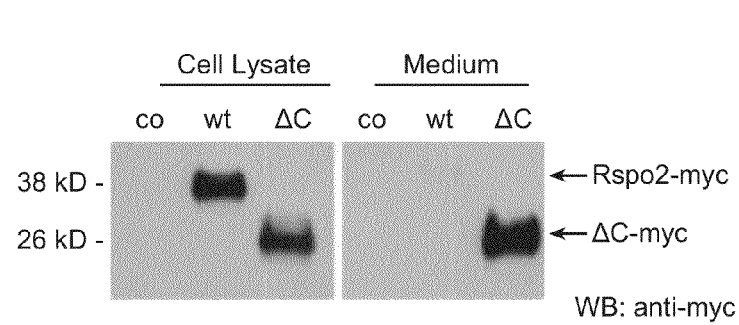
Figure 2C:
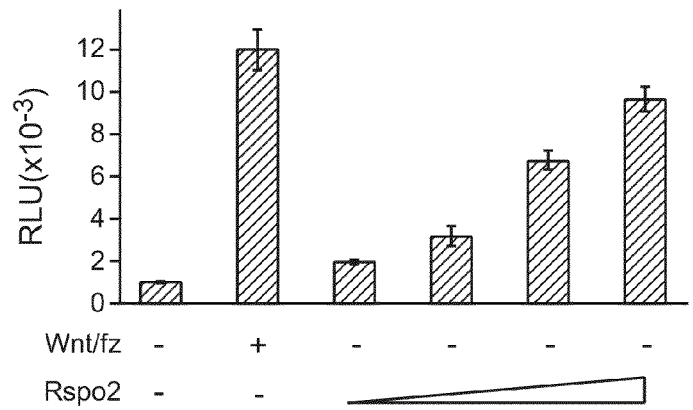
Figure 2D:
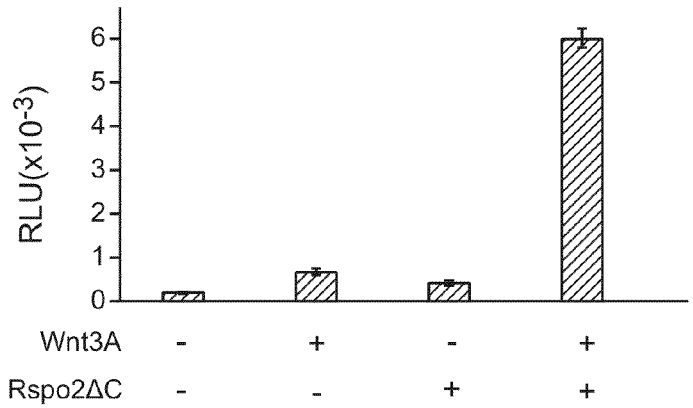
Figure 5A:
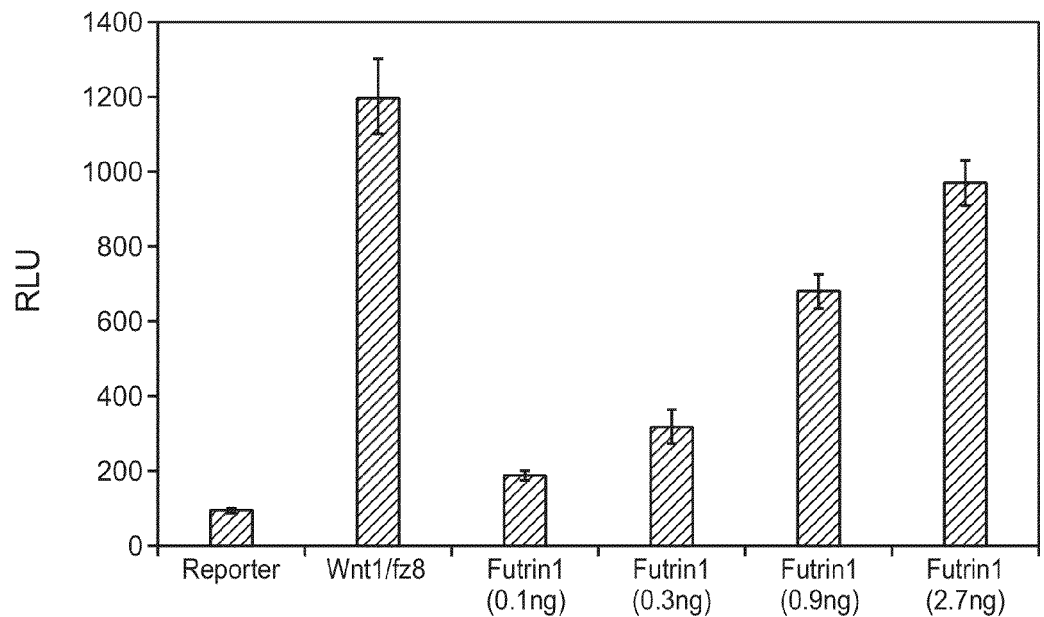
FIG. 5A-B: Futrins promote Wnt signaling. Cotransfection experiments in 293T cells.
Figure 5B:
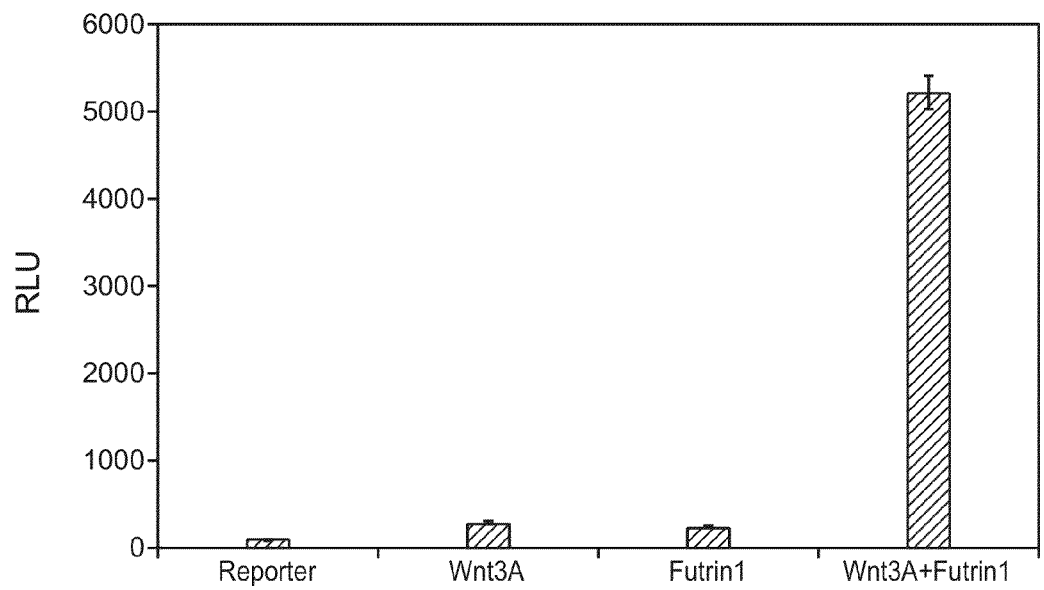

Xenopus Futrin1 and human Futrin1, 2, and 3 are able to stimulate Wnt-responsive reporter expression in HEK 293T cells when provided by transient transfection (FIGS. 2C and 5A). In addition, they are able to enhance reporter expression induced by Wnt (mouse Wnt1/3A) synergistically (FIGS. 2D and 5B). Cotransfection experiments in HEK239T cells were carried out with the indicated genes and the Wnt reporter TOP-FLASH (Korinek et al. Science 275 (1997) 1784-1787) and Renilla-luciferase for normalization, in 96-well plates using FuGENE 6 (Roche). After 24 hours relative luciferase activity was determined.

All tested members of the Rspo family (e.g. murine Rspo1-3, human Rspo2, 3) show equivalent effects (FIG. 6A and data not shown). Rspo2 signalling is sensitive to the Wnt/β-catenin pathway inhibitors dominant negative TCF and dickkopf1 (FIG. 6B). A synergistic signalling effect is observed when Rspo2 is cotransfected with extracellular but not with intracellular components of the Wnt/β-catenin pathway (FIG. 6C). The greatest cooperation is reproducibly seen between Rspo2 and Wnts, either using conditioned media (FIG. 2D) or following co-transfection (FIG. 6C).

Figure 2E:
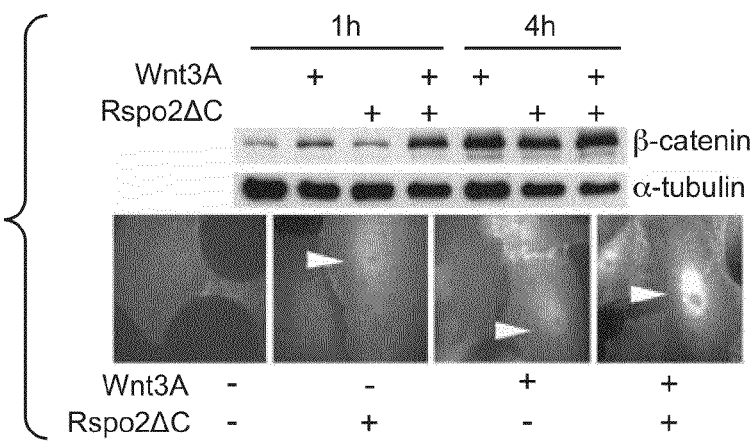
Figure 2F:
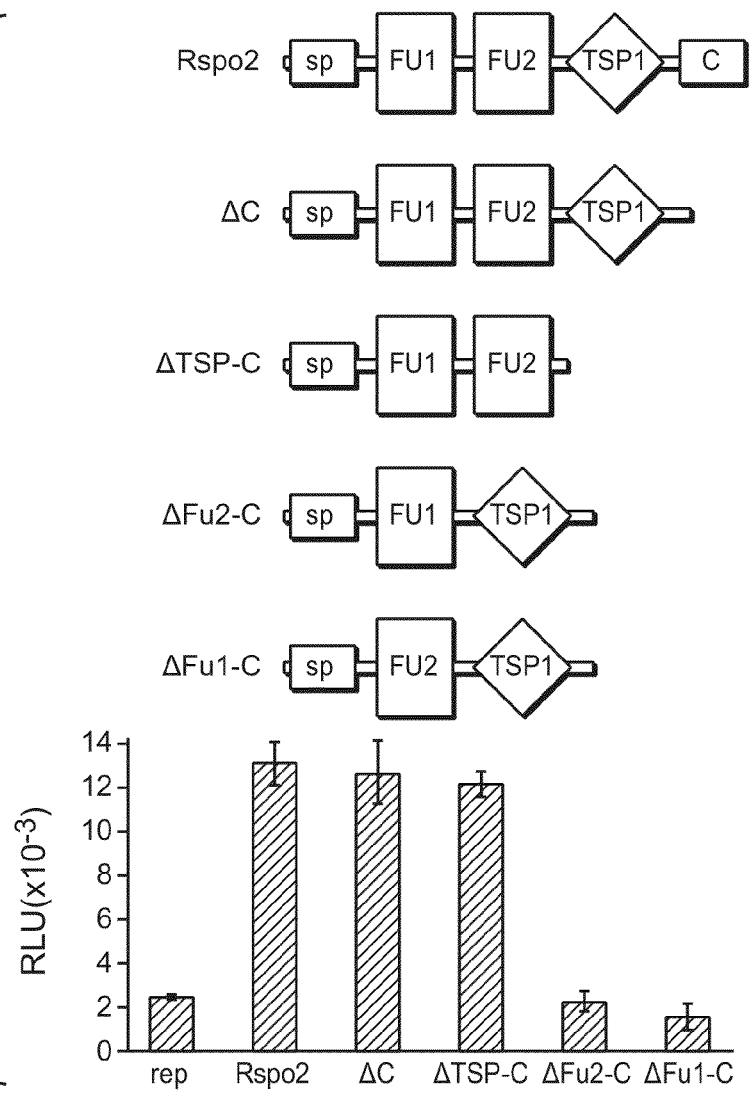

A hallmark of Wnt/β-catenin signalling activation is the cytosolic accumulation of β-catenin due to its stabilisation. Treatment of 293T cells with Wnt3a conditioned medium induces cytosolic β-catenin after 1 hour and while recombinant Rspo2ΔC alone is not able to stabilize β-catenin during this interval, it strongly enhances activity of Wnt3a to do so (FIG. 2E, top). After 4 hours treatment, both Wnt3a and Rspo2ΔC conditioned media are able to induce β-catenin accumulation to similar levels (FIG. 2E, top). β-catenin is known to enter the nuclei in response to Wnt stimulation and activate gene expression together with Lef/Tcf transcription factors. Treatment of SHEP cells by either Wnt3a or Rspo2ΔC conditioned media weakly induces β-catenin nuclear localization, while co-treatment with Wnt3a and Rspo2ΔC strongly enhances nuclear accumulation (FIG. 2E, bottom). It can be concluded that R-spondins represent a novel family of secreted proteins capable promoting Wnt/β-catenin signalling.

To functionally study its signalling domains, serial deletions of Xenopus Rspo2 (FIG. 2F) were created. As discussed, the basic C-terminus can be removed without loss of activity and this is also true for the TSP1 domain (FIG. 2F). However, the furin-like domains are necessary for Wnt/β-catenin signalling since deletion of either the furin-1 or -2 domains abolishes the activity in reporter assays (FIG. 2F).

Example 4

Futrins are Required for Full Wnt Signalling

To test the requirement of Futrins in Wnt signalling, siRNA mediated gene knock-out was utilized (Brummelkamp et al., Science. 2002, 296 (5567): 550-3). Hela cells were transfected using Lipofectamine Plus with 80 ng Wnt reporter 7LEF-Rev-fosLuc, 10 ng pRL-TK (Promega) and 300 ng pSuper constructs (Brummelkamp et al.) that produce either siRNA against human Futrin1 and 2, or a nonsense control. 7LEF-Rev-fosLuc reporter construct containing seven LEF binding sites in front of minimal fos promoter followed by firefly luciferase ORF was kindly provided by R. Grosschedl (Howard Hughes Medical Institute). pSuper constructs contain 19-nucleotide sequences from human Futrin1 (sequence: TCCCATTTGCAAGGGTTGT (SEQ ID NO:17)), human Futrin1 (sequence: AGCTGACTGTGATACCTGT (SEQ ID NO:18)) or control nonsense sequence (ACTACCGTTGT-TATAGGTG (SEQ ID NO:19)).

One day after transfection medium was changed from 10% to 0.5% FCS. Three days after transfection, mouse Wnt3A conditioned medium or control medium from 293 cells was added to the culture to stimulate Wnt signalling. 24 hours later, luciferase activity was determined. As shown in FIG. 7, Hela cells show reduced levels of Futrin 1 and 2, and Wnt signalling dropped by 50%, indicating that Futrins are required for full Wnt signalling. This effect can be efficiently rescued by 5 ng recombinant mouse Futrin 1, attesting its specificity. Data are normalized to Renilla luciferase activity.

Example 5

Expression of R-Spondin Genes in Xenopus and Mouse Embryos

In Xenopus embryos, no maternal Rspo2 RNA is detected by RT-PCR. Its zygotic expression starts at early gastrula stage and remains constant throughout neurulation and organogenesis (FIG. 8A). By whole-mount in situ hybridization, weak expression of Rspo2 is observed throughout the ectoderm of early gastrulae (not shown). During gastrulation strong expression is detected in the marginal zone in both deep and superficial layers, but is excluded from the Spemann organizer (FIG. 8B). At late gastrula stage Rspo2 expression persists in lateral plate mesoderm and becomes detectable in trie anterior neural plate (FIG. 8C). At stage 15 expression is seen in two longitudinal stripes along the neural plate (future roof plate), in the anterior neural plate and in lateral and posterior mesoderm (FIG. 8D). Expression of Rspo2 at tailbud stage (FIG. 8F) is restricted to several regions of the brain, including diencephalon and midbrain-hindbrain boundary, pronephros and dorsal neural tube. Expression is also detected in the dorsal and ventral-most portions of somites, the dorsal fin and the proctodeum. Rspo2 expression in the brain of late tadpoles is mainly restricted to diencephalon, including the zona limitans intrathalamica (zli) (FIG. 8H).

Xenopus Rspo3 expression is related to that of Rspo2. It is first detected at gastrula stage (not shown) and in neurulae it is expressed in the anterior border of the neural plate and posterior mesoderm (FIG. 8E). At tail bud stage, it is coexpressed with Rspo2 in the central nervous system but shows additional expression in branchial arches and the tailbud (FIG. 8G).

In mouse, Rspo3 transcripts are detected by in situ hybridization at day 7.5 in the primitive streak (FIG. 8J) while expression of Rspo1 and 2 is not detectable. At day 9.5, Rspo1-3 show differential expression in various neural and mesodermal derivatives (FIG. 8K-M), mainly along dorsal neural tube (Rspo1 and 3), diencephalon (Rspo1, 2, 3), somites (Rspo3) and tailbud mesoderm (Rspo3). In limb buds all three genes show prominent differential expression (FIG. 8I), particularly, in the morphogenetically active region such as the apical ectodermal ridge (AER) (Rspo2).

Example 6

R-Spondins are Co-Expressed with and Regulated by Wnts

Figure 9A:
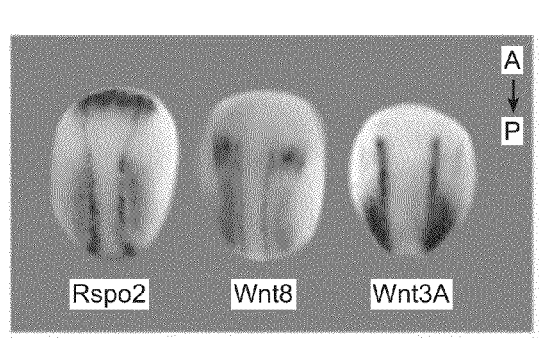
FIG. 9A-E: Regulation of *Xenopus* R-spondins by Wnt signaling.

R-spondins not only show functional interaction with Wnt signalling, but also co-expression with Wnt genes in many regions during *Xenopus* and mouse embryonic development. In gastrula mesoderm of both *Xenopus* and mouse, Rspo2 and -3 are co-expressed with XWnt8 and mWnt3, respectively. Similarly, at later stages, R-spondin family members are widely co-expressed with a number of Wnt genes e.g. in midbrain-hindbrain boundary, dorsal neural tube and limb bud and tail bud. A direct comparison between the expression patterns of *Xenopus* Rspo2 and Wnt8 and Wnt3a shows a large overlap (FIG. 9A).

Figure 9B:
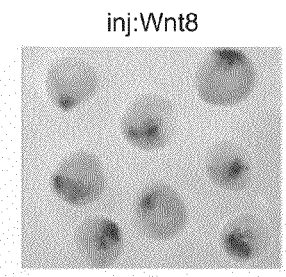
Figure 9C:
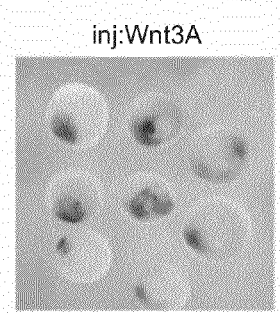
Figure 9D:
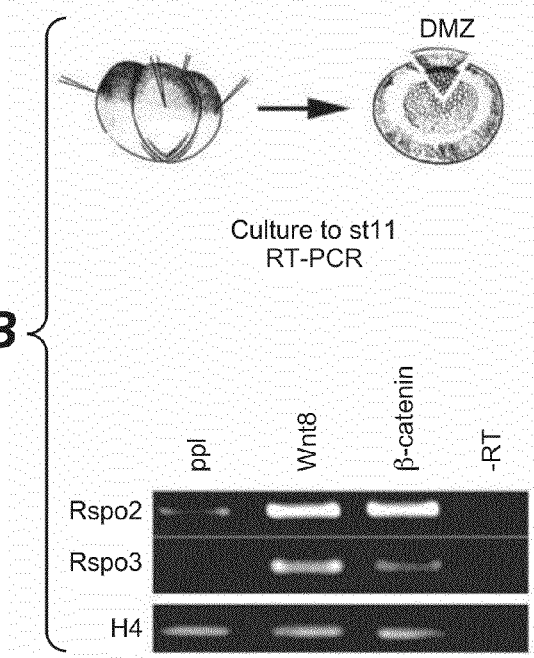
Figure 9E:
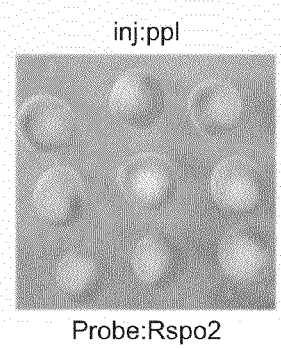

Indeed, Wnts are able to induce Rspo expression since *Xenopus* embryos injected with pCS-Wnt8 or pCS-β-catenin DNA upregulate both Rspo2 and Rspo3 by RT-PCR (FIG. 9B).

Likewise, embryos injected with pCS-Wnt8 or pCS-Wnt3a DNA show ectopic Rspo2 expression by in situ hybridization (FIG. 8C-E). The results indicate that the observed co-expression is due to regulation of R-spondins by Wnts. This is consistent with the observation that Rspo1 expression is reduced in dorsal spinal cord of Wnt1 or Wnt3a knockout mouse embryos.

Example 7

Figure 10A:
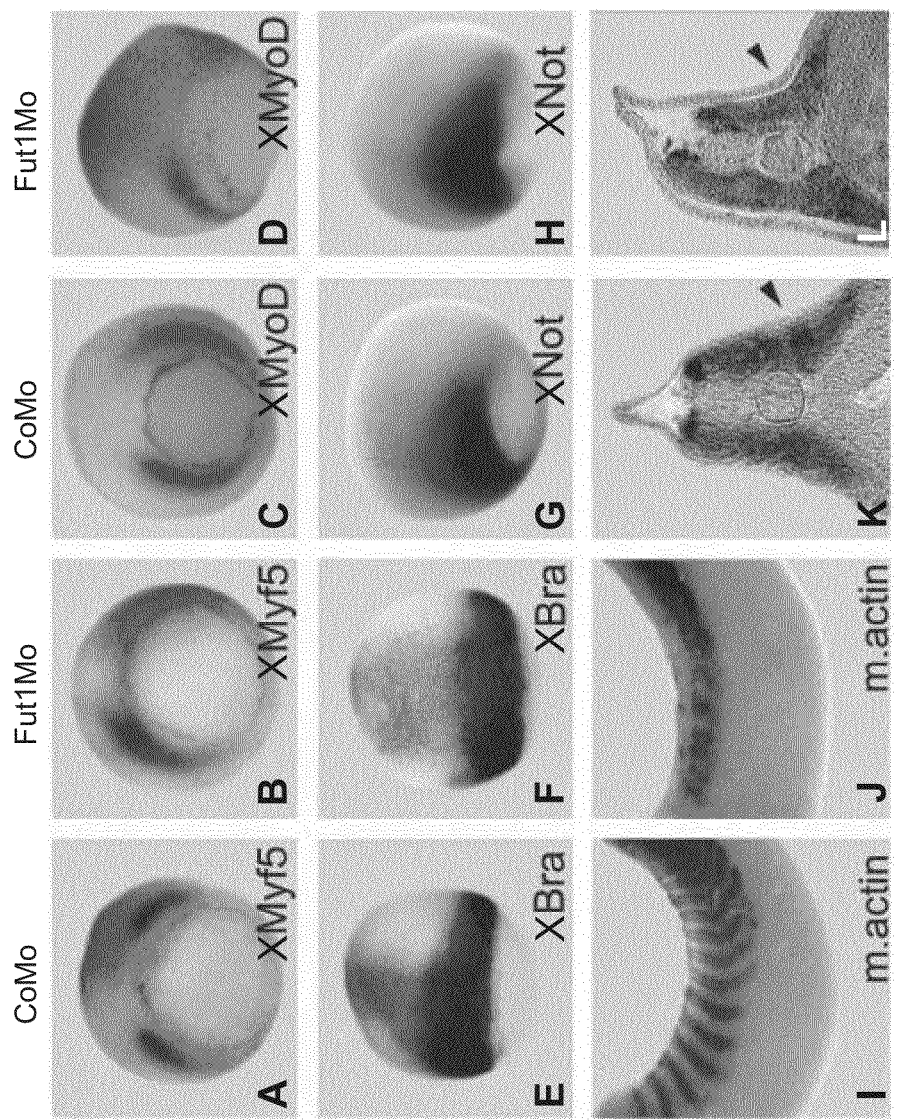
FIG. 10A-C: Futrin 2 is required for muscle formation.
Figure 10B:
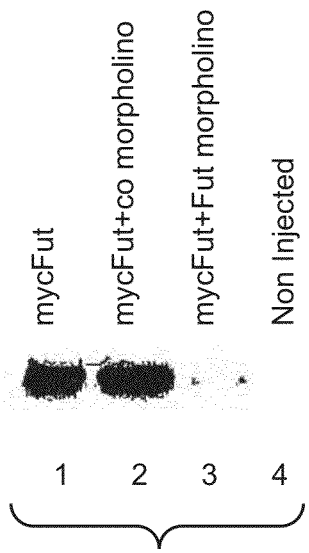
Figure 10C:
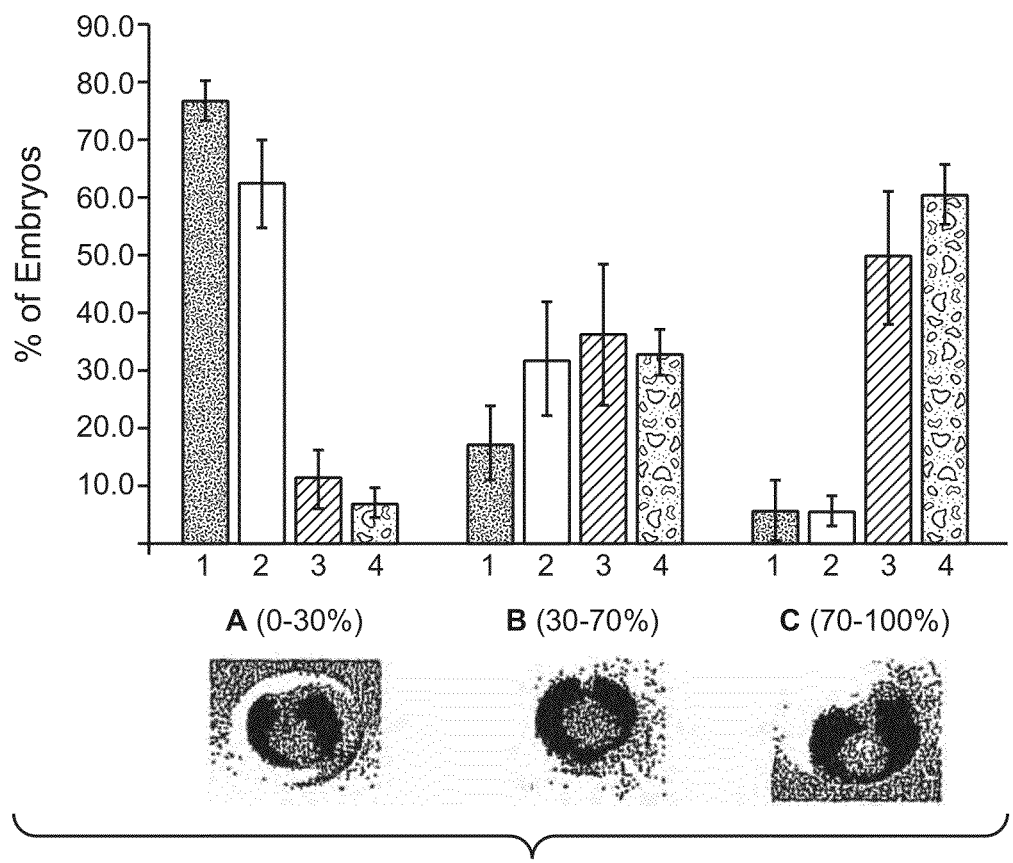

Futrin 1 (R-Spondin 2) Activates Neural Markers and Regulates (Promotes) Muscle Formation Loss-of-function analysis in *Xenopus* embryos show that Futrin 1 is required for muscle formation. Injections of antisense morpholino oligo against futrin 1 (Fut1-Mo) cause downregulation of early muscle markers MyoD and Myf5 and induce muscle defects (FIG. 10A). The specificity of this effect was documented, first, by the ability of Fut1-Mo to inhibit translation of the cognate DNA construct when overexpressed in embryos (FIG. 10B) and, second, by the ability of XFut1mRNA to rescue the effect of Fut1-Mo (FIG. 10C).

When the Wnt/(β-catenin pathway is overactivated in *Xenopus* embryos a variety of responses are observed: i) mRNA injection of pathway activators typically induces secondary embryonic axes in whole embryos and anterior neural markers in animal caps and whole embryos; ii) DNA injection of pathway activators driving expression after MBT, posteriorizes the central nervous system (CNS). To test if Rspo2 is able to mimic any of these effects synthetic mRNA was microinjected in *Xenopus* embryos. However, Rspo2 mRNA injection does not induce secondary axes in whole embryos and injection of pCS-Rspo2 DNA does not posteriorize CNS, since heads are normal sized, Otx2 expression is expanded and en2 unaffected (FIG. 11D, H).

Figure 11K:
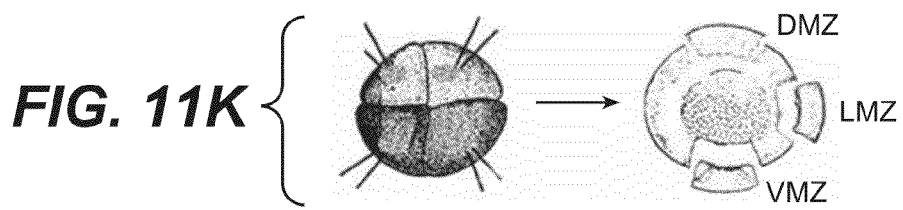
Figure 11L:

In animal caps Rspo2 induces the pan-neural markers NCAM and N-tubulin and the anterior neural marker, Otx2, as do Xwnt6 and β-catenin (FIG. 11A). Similarly, in whole embryos injected with Rspo2 mRNA, ectopic cement glands and lateral expansion of the neural plate are observed at the injected side, as shown by expression of neural markers Sox3, Otx2, not2, en2 and Rx1 (FIGS. 11B-H). Ectopic Otx2 expression is observed already in gastrula stage embryos (FIG. 11I+J). These results are consistent with the ability of Wnt/β-catenin signalling to block BMP4 expression and thereby to activate neural development.

To further analyze the mRNA overexpression effect of Rspo2 an BMP4, Activin, Nodal and FGF signaling, animal cap assays were carried out and tested for the induction of target genes by three growth factor signals (FIG. 12). Rspo2 expectedly blocks BMP4 mediated Xvent2 expression but surprisingly also inhibits Activin and Nodal mediated Xbra induction (FIG. 12A-C). This is unlike XWnt8 and β-catenin mRNA injections, which do not affect Xbra induction by Activin (FIG. 12B). In contrast to signaling by three TGF-β type growth factors, FGF8 induced Xbra expression is unaffected by overexpressed Rspo2 (FIG. 12D). It can be concluded that Rspo2 overexpression in addition to activating the Wnt/β-catenin pathway, is also able to interfere with signaling by three TGF-β family growth factors.

Figure 11M:
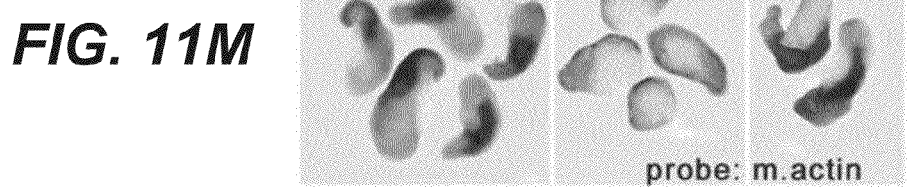
Figure 11N:
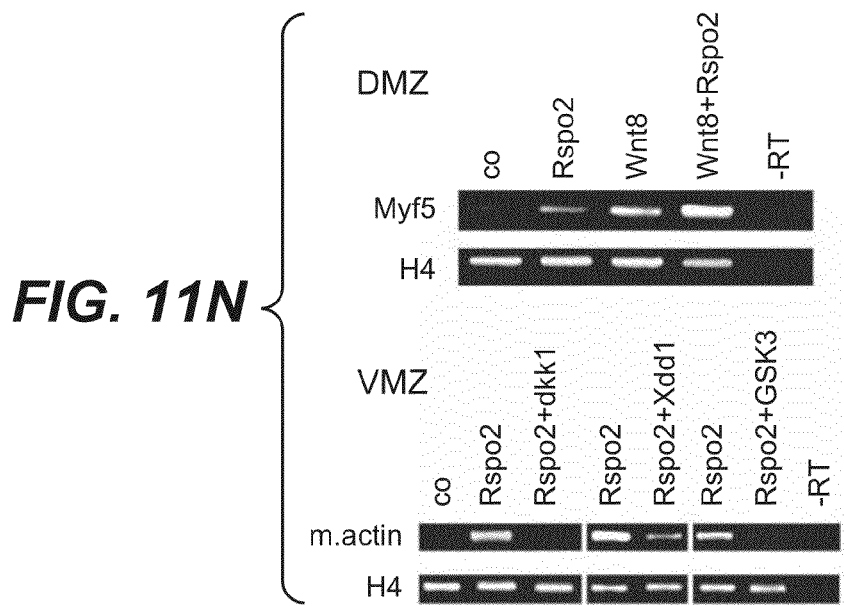
Figure 12A:
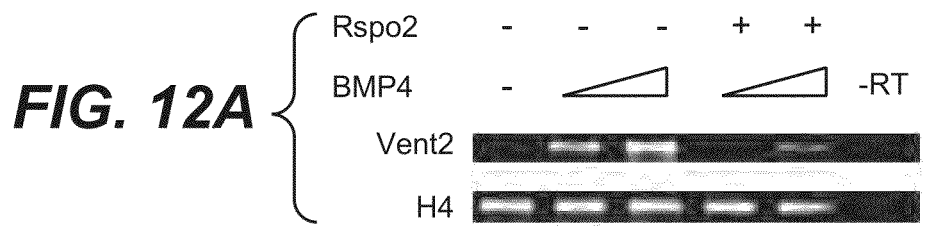
FIG. 12A-D: Rspo2 interferes with BMP-4, Activin and Nodal but not with FGF in *Xenopus*.
Figure 12B:
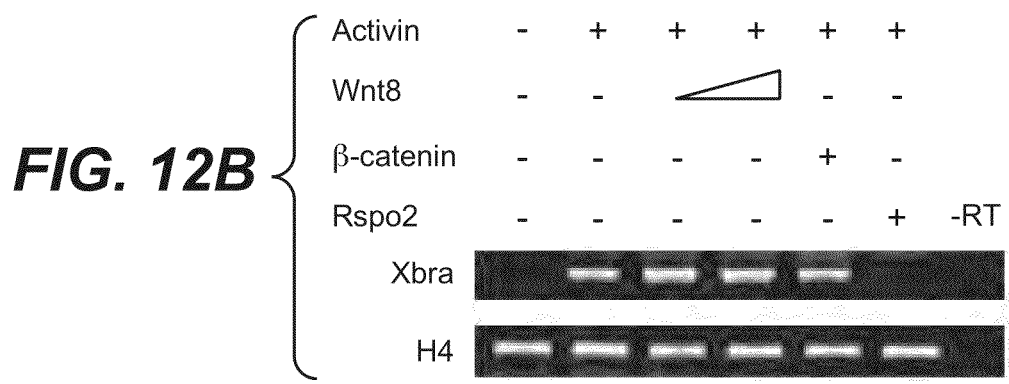
Figure 12C:
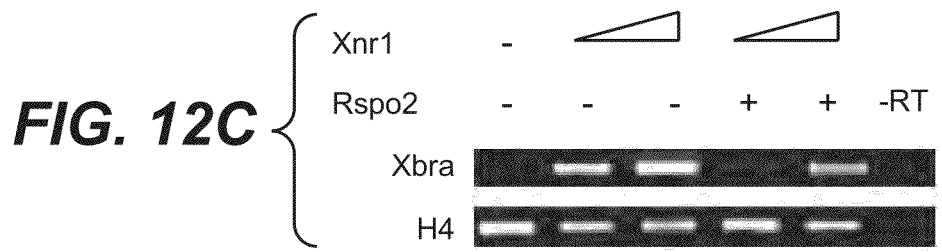
Figure 12D:
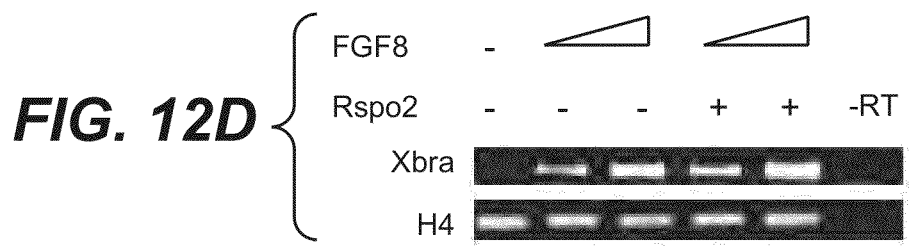

Another well known effect of zygotic Wnt/β-catenin signalling is its ability to promote myogenesis. For example, XWnt8 can induce muscle formation in ventral mesodermal cells. When ventral marginal zones (VMZs) from Rspo2 injected embryos are dissected and cultured until stage 40, they elongate, form tail like structures, and are contractile. This phenotype is indistinguishable from control lateral marginal zone explants (LMZs), which typically differentiate muscle (FIG. 4K-L). In situ hybridization confirmed induction of muscle actin in both Wnt8 and Rspo2 injected VMZs but not in control (preprolactin-injected) VMZs (FIG. 11M). Since R-spondins are able to enhance Wnt signalling in 293T cells, their cooperation in *Xenopus* myogenesis was tested. Myf5 is a myogenic marker characteristically expressed in lateral mesoderm. However, it is excluded from dorsal mesoderm, and dorsal marginal zone (DMZ) explants express only little myf5 as determined by RT-PCR (FIG. 11N). In DMZs from embryos injected with DNA constructs driving post MBT expression, myf5 is weakly induced by Rspo2, moderately by Wnt8 and strongly by their combination (FIG. 11N, top). The myogenesis promoting effect of Rspo2 is repressed by dominant negative dishevelled (Xddl), dkkl and GSK-3β, which all block Wnt signalling (FIG. 11N, bottom). In summary, the results suggest that Rspo2 can promote myogenesis via the Wnt/β-catenin pathway.

Example 8

R-Spondin2 is Required for Wnt/β-Catenin-Mediated Myogenesis

Figure 13C:
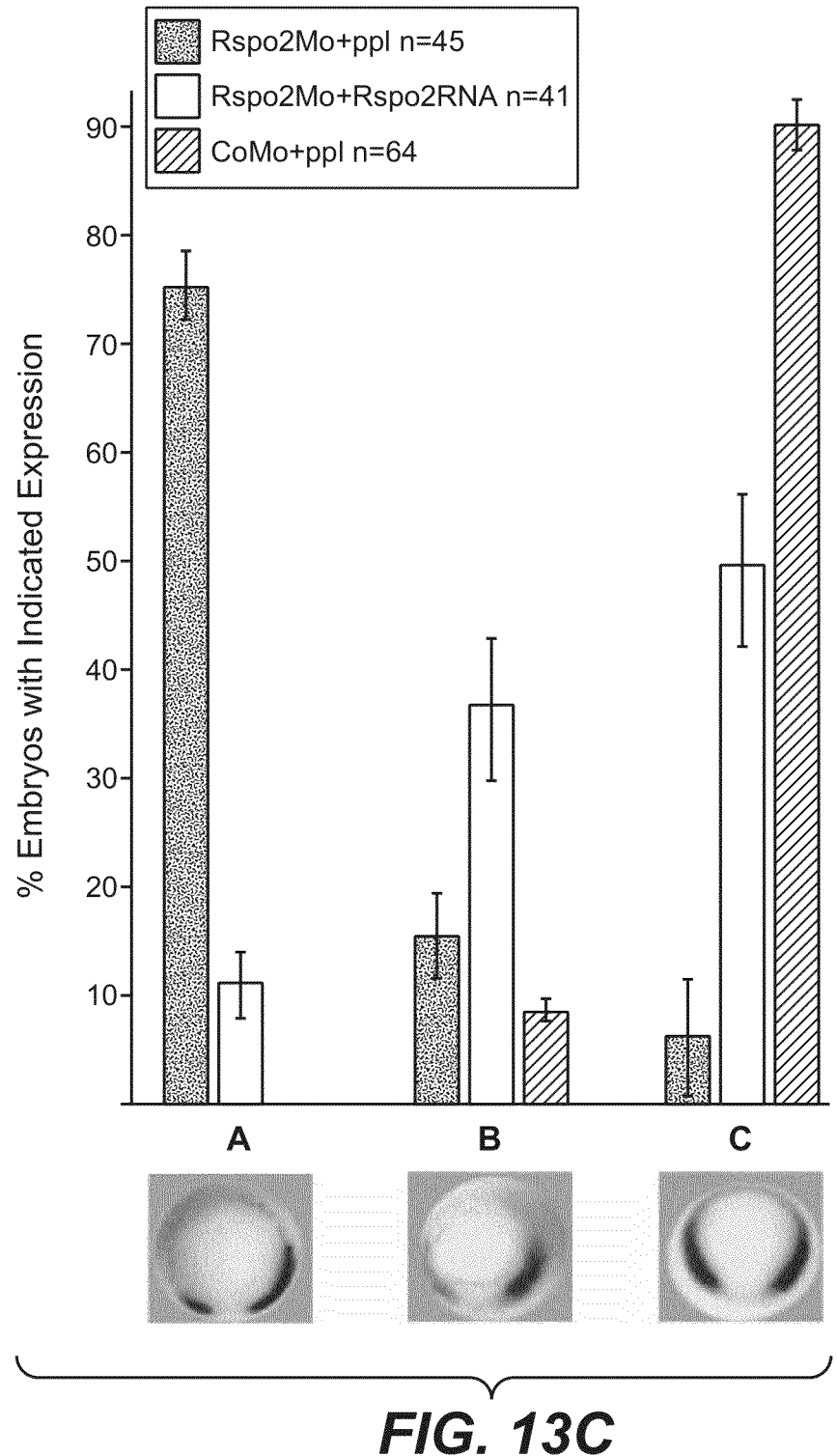

To investigate the physiological role of Rspo2 during *Xenopus* embryogenesis, antisense morpholino oligonucleotides were injected (Rspo2Mo). The ability of Rspo2Mo to block Rspo2 protein production is demonstrated by Western blot (FIG. 13A). Injection of this Morpholino into one dorso-animal blastomere at eight cell stage results in eye defects, although the expression of early eye-(Rx1, Pax6), anterior neural (Otx2) and pan-neural markers (Sox3) is not obviously affected (not shown).

Equatorial Injection of Rspo2Mo in one blastomere at eight cell stage leads to muscle defects at the injected side (FIG. 13B). In situ hybridisation for muscle actin and transverse trunk sections show that Rspo2Mo injection causes disorganized somites (panels a-b) and reduced myotomes (panels c-d). Lineage tracing experiments showed that Rspo2Mo injected cells contribute to lateral plate mesoderm instead of somites or undergo cell death (data not shown). At gastrula stage expression of the myogenic markers myf5 and myoD is strongly down-regulated at the Rspo2Mo injected side (panels e-h), while the pan-mesodermal marker Xhra and the organizer marker Xnot2 are unaffected (panels i-i).

To test the specificity of Rspo2Mo, rescue experiments were performed by co-injecting Rspo2Mo together with a Rspo2 RNA, in which six non-coding nucleotides were mutated so that it would not be targeted by this Morpholino. Expression of myf5 (FIG. 13C) and myoD (data not shown) is effectively rescued by this mutant Rspo2 RNA, indicating that the effect of Rspo2Mo an myogenesis is specific.

Figure 13D:
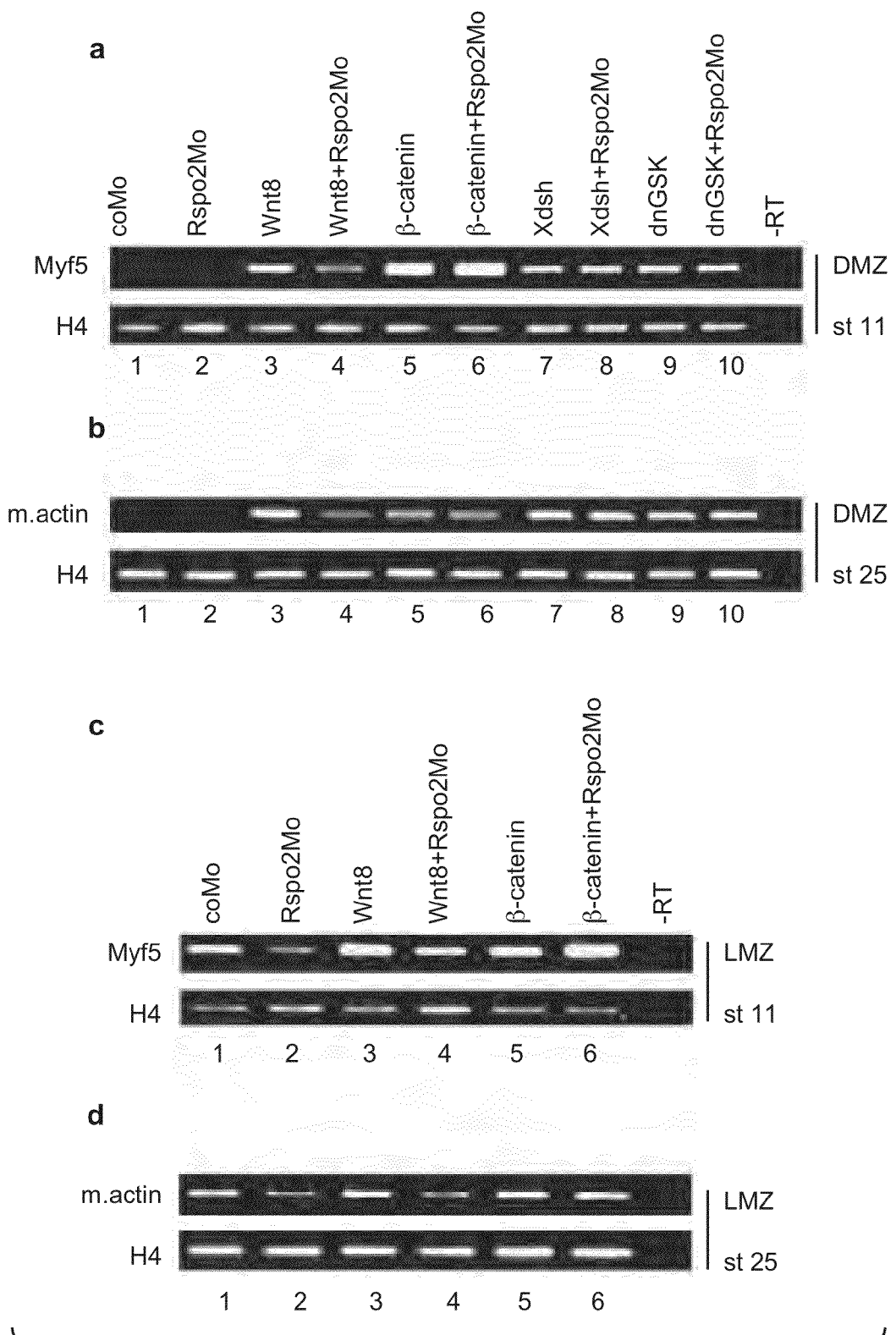

Rspo2Mo was used as a tool to examine the epistatic position of Rspo in the Wnt/(β-catenin pathway. As read out for Wnt/β-catenin signalling the expression of myf5 and muscle actin in marginal zone explants was used (FIG. 13D). In DMZ and VMZ explants, Wnt8 DNA induces myf5 and muscle actin and this induction is significantly blocked by Rspo2Mo (FIG. 13D, panels a-b, lanes 3-4). However, myf5 and muscle actin induction by intracellular activators of the Wnt pathway like dishevelled, dnGSK-36 and β-catenin is unaffected by Rspo2Mo (a-b, lanes 5-10). In LMZ explants, Rspo2Mo Injection down-regulates endogenous myf5 and muscle actin expression (FIG. 13D, panels c-d, lanes 1-2). In DNA coinjections this effect is rescued effectively by β-catenin—but only poorly by XWnt8 (lanes 3-6). The residual effect of XWnt8 is likely due to its non-cell autonomous action an cells that did not receive Rspo2Mo. Taken together these results indicate that Rspo2 affects the Wnt/(β-catenin pathway at the level or upstream of dishevelled.

Example 9

R-Spondins are Required for Wnt/β-Catenin Signalling in HeLa Cells

Figure 14A:
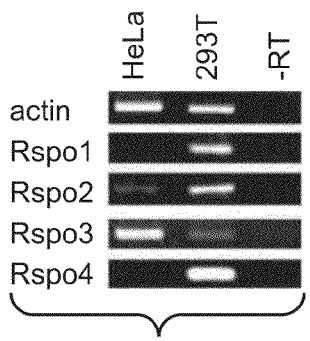
FIG. 14A-D: R-spondins are required for Wnt signalling in HeLa cells.
Figure 14B:
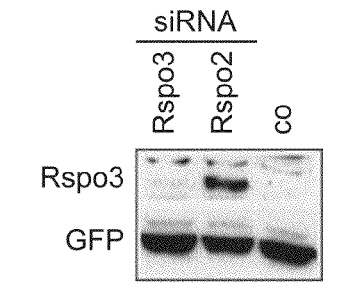

Next the requirement of Rspo2 for Wnt signalling was tested in mammalian cells using siRNA. Since there are four R-spondins with apparently redundant function, HeLa cells were selected, that only express Rspo3 and very weakly Rspo2 (FIG. 14A). Various other cell lines, such as 293T cells, express all four genes, complicating a siRNA approach.

siRNA mediated gene knock-down was carried out by transfecting pSUPER constructs (Brummelkamp et al., Science 296 (2002), 3286-3305) to produce siRNAs targeted against Rspo2 and -3 (siRNA Rspo 2, 3). As control, a nonsense siRNA was used. To test the efficiency of siRNA, FLAGtagged human Rspo3 was co-transfected with siRNAs and its production was repressed by siRNA Rspo3 but not siRNA Rspo2 (FIG. 14B).

Figure 14C:
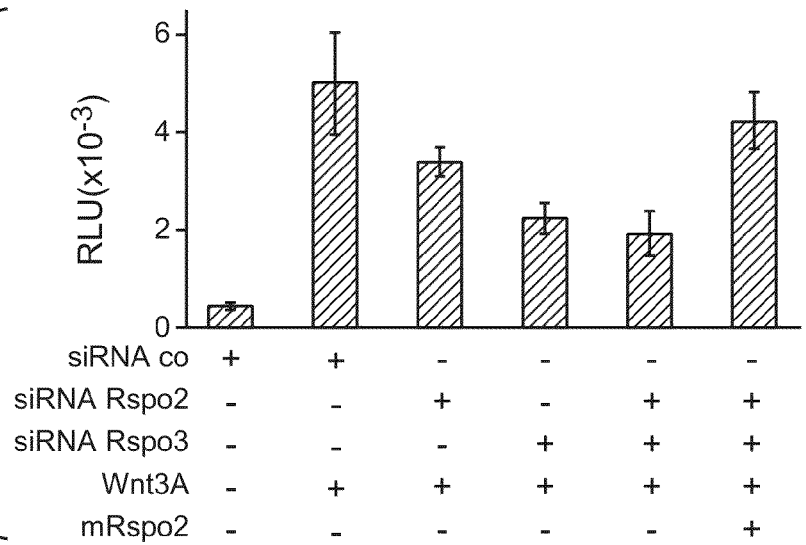
Figure 14D:
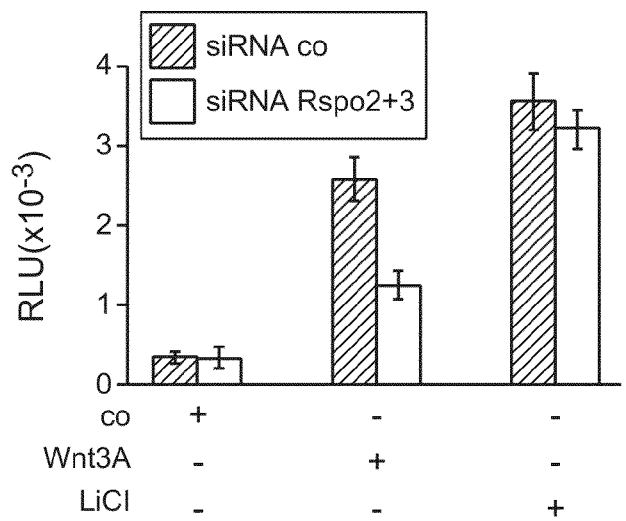
Figure 15A:
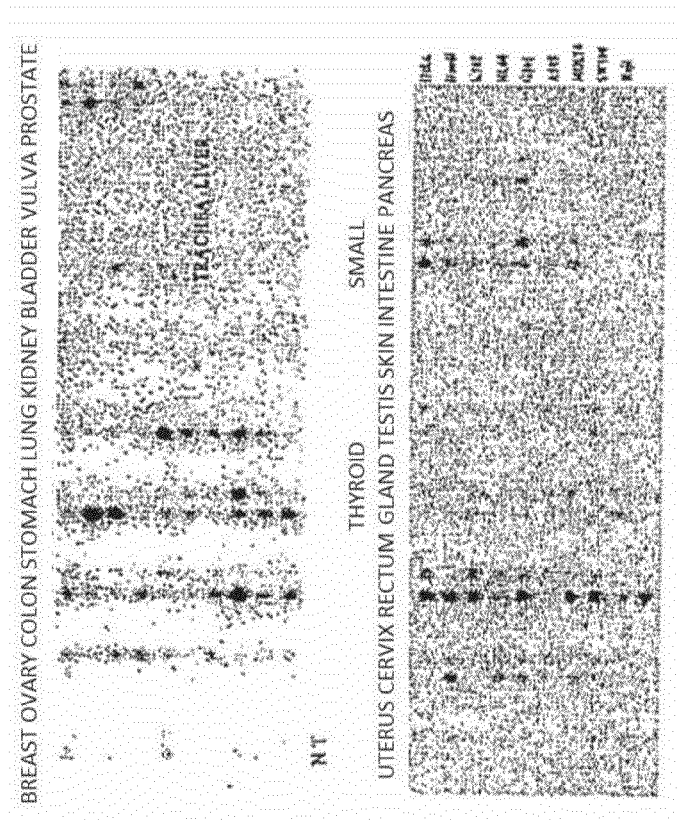
FIG. 15A-E: Futrin expression is deregulated in various human tumors.
Figure 15B:
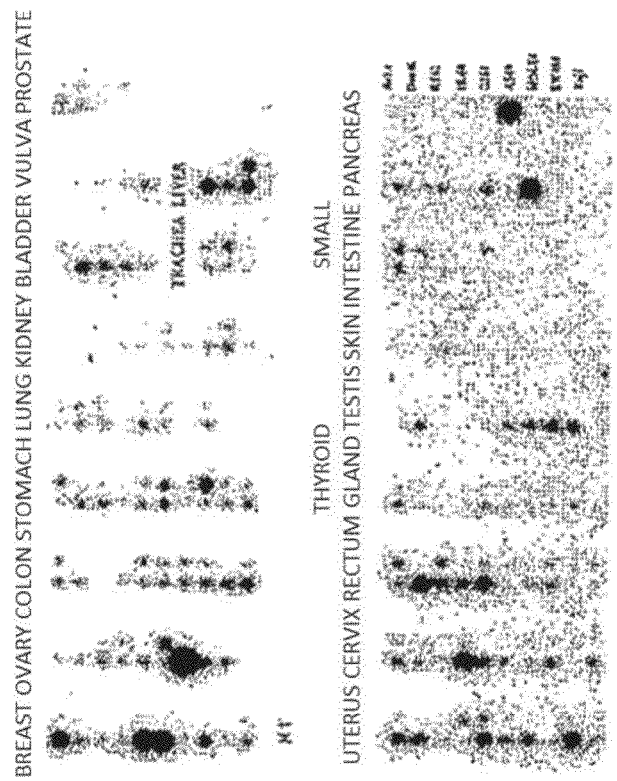
Figure 15C:
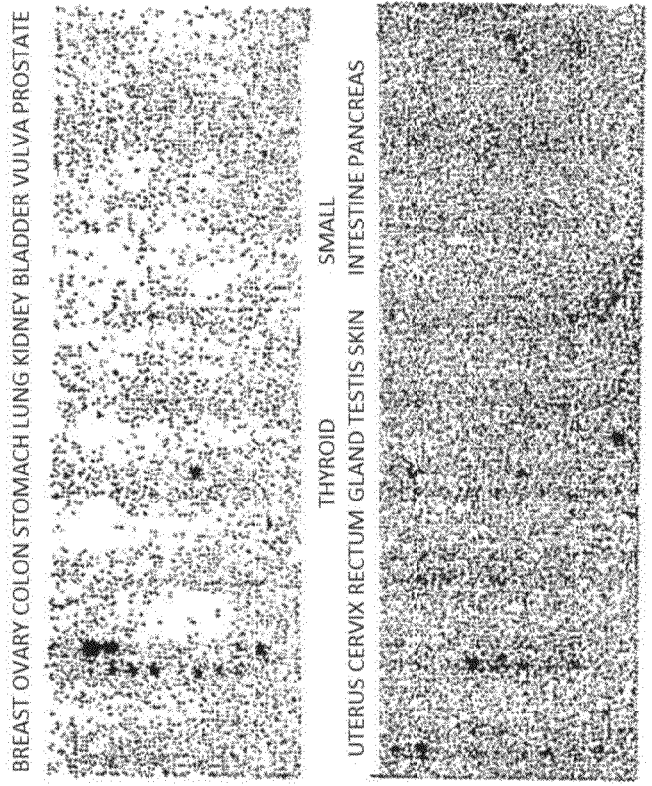
Figures 15D, 15E:
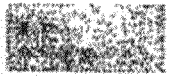

In Wnt-reporter assays, both siRNA Rspo2 and -3 decreased Wnt3a-induced luciferase activity compared to control siRNA (FIG. 14C). When siRNA Rspo2 and -3 are co-transfected, reporter activity drops to 40%. This effect is specific since the decreased Wnt signalling can be rescued by co-transfected mouse Rspo2, which is not targeted by siRNAs against human R-spondins (FIG. 14C). Furthermore, unlike Wnt3a-induced reporter activity, siRNA Rspo2+3 do not affect Li+-induced Wnt/(β-catenin signalling (FIG. 14D). Since Li+ acts by inhibiting GSK3β activity, this is again consistent with Rspo2 acting at the level or upstream of dishevelled. conclude that in HeLa cells R-spondins are required for full Wnt/(β-catenin signalling.

Example 10

Futrin Expression is Deregulated in Human Tumors

Figure 16:
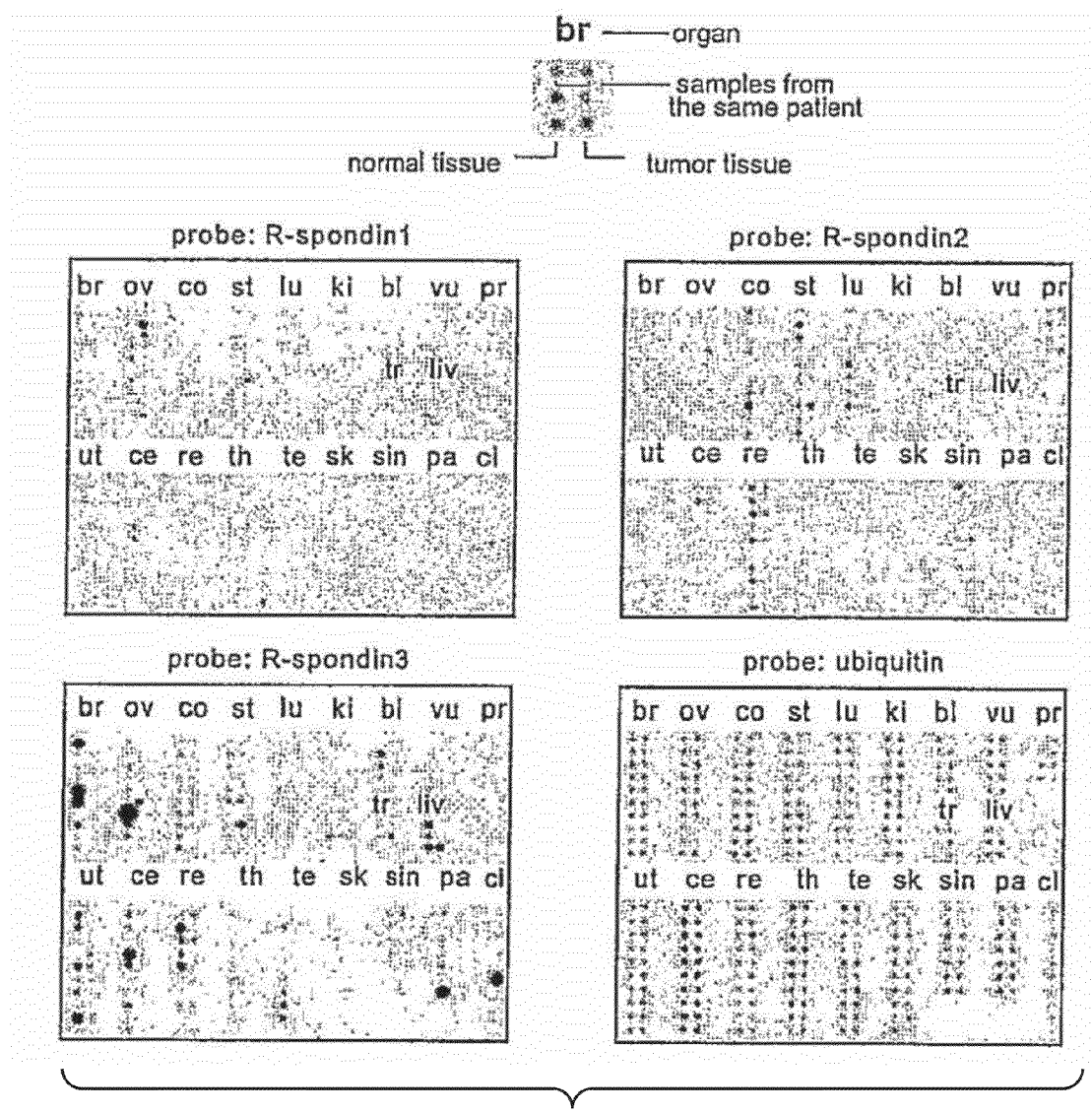
FIG. 16: Expression of human R-spondins in tumor samples. Dot blot analysis of human Rspo1, 2 and 3 in normal and tumour samples. The same CDNA samples (Cancer Profiling Array II, Clontech) were hybridized with human Rspo1, 2, 3 and ubiquitin probes, (top) The Cancer Profiling Array contains pairs of cDNAs from tumor and corresponding normal tissue samples from individual patients and spotted side-by-side as indicated. Organ abbreviations are: Br, breast; ov, ovary; co, colon; st, stomach; lu, lungs; kidney; bi, bleeder, vu, vulva; pr, prostate; tr, trachea; liv, liver; ut, uterus; ce, cervix; re, rectum; th, thyroid gland; te, testis; sk, skin; sin, small intestine, pa, pancreas.
Figure 17A:
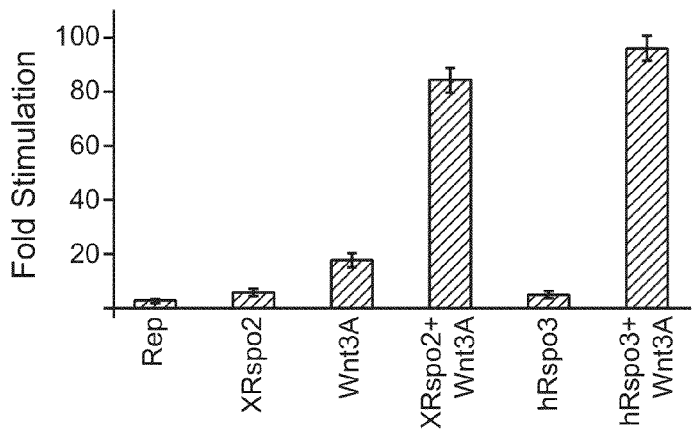
FIG. 17A-C: Interaction of R-spondins with components of the Wnt/β-catenin signalling pathway.
Figure 17B:
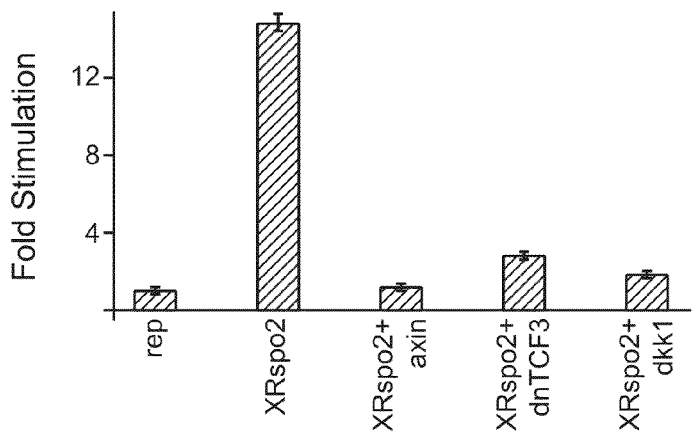
Figure 17C:
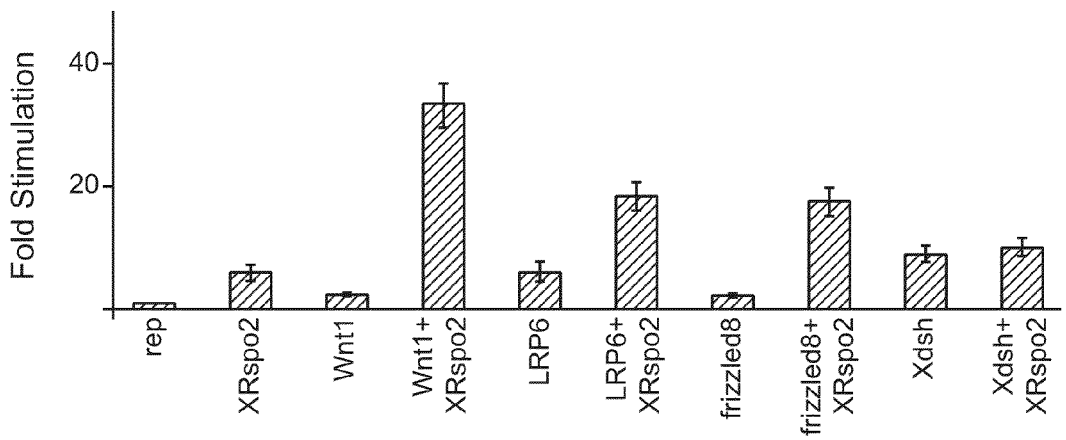

Misregulation of Wnt/β-catenin signalling is implicated in tumorigenesis, e.g., colon cancer, breast cancer and melanoma (Barker et al., 2000; Bienz and Clevers, 2000; Polakis, 2000). Since R-spondins (futrins) promote Wnt/β-catenin signalling they may also play a role in tumorigenesis. Thus, the expression of Futrin 1-4 in various normal and cancerous human tissues was studied using radioactive hybridisation on Clontech Cancer Profiling Array II. Hybridization with ubiquitin probe was used for normalisation. The results show that expression of Futrins 1-3 is dramatically deregulated in cancerous human tissues (FIG. 15). In most of the tumors the expression of Futrins 1-3 is dramatically decreased (colon, stomach, lung, rectum tumors for Futrin 1, breast, ovary, bladder, uterus, cervix, rectum tumors for Futrin 2, uterus and cervix tumors for Futrin 3). In a few cases the expression of Futrin 1-3 is upregulated (one case of stomach tumor for Futrin 1 and 2, ovary tumor for Futrin 3). Futrin 4 shows very low level of expression in most of the tissues studied, except ovary. Further results are shown in FIG. 16 also showing that HRspo1 is weakly expressed in adult organs. It shows upregulation in ovary tumours from two patients and in one stomach tumour sample. HRspo2 is expressed in organs of endodermal origin, including colon, rectum, small intestine and lung. Its expression decreased in corresponding tumour samples. HRspo3 is expressed widely and decreases in many tumour samples. In general, the expression of hRspo1-3 is deregulated in a number of tumours, while hRspo4 expression is very weak both in human adult organs and tumours (data not shown).

The invention claimed is:

1. A method of determining whether a binding partner of a Futrin 1 polypeptide affects Wnt signaling activity, the method comprising:
   (a) providing a mammalian cell in culture comprising the Futrin 1 polypeptide and a Wnt inducible reporter, wherein the Futrin 1 polypeptide comprises the amino acid sequence of SEQ ID NO:26, the amino acid sequence of amino acids 21-243 of SEQ ID NO:26, the amino acid sequence of amino acids 1-146 of SEQ ID NO:26, or the amino acid sequence of amino acids 21-146 of SEQ ID NO:26, wherein the Futrin 1 polypeptide is able to promote Wnt signaling; and
   (b) detecting the level of reporter expression in the cell in the presence and absence of the binding partner, wherein a change in the level of reporter expression indicates that the binding partner affects the Wnt signaling.

2. The method of claim 1, wherein the Futrin 1 polypeptide comprises the amino acid sequence of amino acids 21-243 of SEQ ID NO:26.

3. The method of claim 1, wherein the Futrin 1 polypeptide comprises SEQ ID NO:26.

4. The method of claim 1, wherein the Futrin 1 polypeptide comprises the amino acid sequence of amino acids 1-146 of SEQ ID NO:26.

5. The method of claim 1, wherein the Futrin 1 polypeptide of comprises the amino acid sequence of amino acids 21-146 of SEQ ID NO:26.

6. The method of claim 1, wherein the change is a decrease in the level of reporter expression and the decrease indicates that the binding partner is an antagonist of Wnt signaling.

7. The method of claim 6, wherein the binding partner is an antibody.

8. The method of claim 7, wherein the antibody is a monoclonal antibody.

9. The method of claim 8, wherein the monoclonal antibody is a chimeric or a humanized antibody.

10. The method of claim 9, wherein the Futrin 1 polypeptide comprises the amino acid sequence of amino acids 21-243 of SEQ ID NO:26.

11. The method of claim 9, wherein the Futrin 1 polypeptide comprises SEQ ID NO:26.

12. The method of claim 9, wherein the Futrin 1 polypeptide comprises the amino acid sequence of amino acids 1-146 of SEQ ID NO:26.

13. The method of claim 9, wherein the Futrin 1 polypeptide comprises the amino acid sequence of amino acids 21-146 of SEQ ID NO:26.

14. The method of claim 1, wherein the change is an increase in the level of reporter expression and the increase indicates that the binding partner is an agonist of Wnt signaling.

* * * * *